United States Patent
Wong et al.

(10) Patent No.: US 9,133,237 B2
(45) Date of Patent: Sep. 15, 2015

(54) CYCLIC PEPTIDES WITH AN ANTI-PARASITIC ACTIVITY

(75) Inventors: Yung-Sing Wong, Saint Martin-d'Hères (FR); Mohamed-Ali Hakimi, Grenoble (FR); Alexandre Bougdour, Grenoble (FR); Hervé Pelloux, Bernin (FR); Danièle Maubon, Saint Ismier (FR)

(73) Assignees: UNIVERSITE JOSEPH FOURIER (GRENOBLE 1) (FR); CENTRE NATIONAL DE LA RECHERCHE SCIENTIFIQUE (FR); (INSERM) INSTITUT NATIONAL DE LA SANTE ET DE LA RECHERCHE MEDICALE (FR)

( * ) Notice: Subject to any disclaimer, the term of this patent is extended or adjusted under 35 U.S.C. 154(b) by 35 days.

(21) Appl. No.: 13/263,309

(22) PCT Filed: Apr. 6, 2010

(86) PCT No.: PCT/FR2010/050658
§ 371 (c)(1), (2), (4) Date: Oct. 26, 2011

(87) PCT Pub. No.: WO2010/116085
PCT Pub. Date: Oct. 14, 2010

(65) Prior Publication Data
US 2012/0034593 A1 Feb. 9, 2012

(30) Foreign Application Priority Data

Apr. 6, 2009 (FR) .................................... 09 52244

(51) Int. Cl.
| | | |
|---|---|---|
| A61K 38/07 | (2006.01) | |
| A61K 38/12 | (2006.01) | |
| C07K 5/10 | (2006.01) | |
| C07K 5/12 | (2006.01) | |
| C07K 7/64 | (2006.01) | |
| C07K 1/107 | (2006.01) | |
| A61K 38/00 | (2006.01) | |

(52) U.S. Cl.
CPC ................. *C07K 5/126* (2013.01); *A61K 38/07* (2013.01); *A61K 38/12* (2013.01); *C07K 1/107* (2013.01); *C07K 1/1075* (2013.01); *C07K 1/1077* (2013.01); *C07K 5/12* (2013.01); *A61K 38/00* (2013.01)

(58) Field of Classification Search
CPC ........ C07K 5/126; C07K 5/12; C07K 1/1077; C07K 1/1075; C07K 1/107; A61K 38/12; A61K 38/07; A61K 38/00
USPC ......................................................... 530/333
See application file for complete search history.

(56) References Cited

U.S. PATENT DOCUMENTS 5,641,769 A 6/1997 Remington et al.

FOREIGN PATENT DOCUMENTS

| JP | 7-196686 A | | 8/1995 | |
|---|---|---|---|---|
| WO | WO01/07042 | * | 2/2001 | ........... A61K 31/395 |
| WO | 03/057722 A2 | | 7/2003 | |

OTHER PUBLICATIONS

Xie et al., Organic Letters (2005) 7(13), 2775-2777.*
International Preliminary Report on Patentability and Written Opinion issued Oct. 18, 2011 by Bureau International de l'OMPI re: PCT/FR2010/050658.
International Search Report issued Jul. 27, 2010 by European Patent Office re: PCT/FR2010/050658.
Beatrice Quiclet-Sire et al. "Powerful carbon—carbon bond forming reactions based on a novel radical exchange process" Chemistry, Aug. 7, 2006, pp. 6002-6016, vol. 12, No. 23, Weinheim an der Bergstrasse Germany.
Beatrice Quiclet-Sire et al. "The Degenerative Radical Transfer of Xanthates and Related Derivatives: An Unusually Powerful Tool for the Creation of Carbon Carbon Bonds", Chemistry, Springer, Jan. 1, 2006, pp. 201-236, vol. 264, Berlin DE.
Katherine T. Andrews, et al. "Targeting histone deacetylase inhibitors for anti-malarial therapy", Medicinal Chemistry, Feb. 2009, pp. 292-308, vol. 9, No. 3.
D. Maubon, et al. "Drug inhibition of HDAC activity: effect on the parasite *Toxoplasma gondii* and chemotherapy perspectives", Clinical Microbiology and Infection, May 2009, p. 301, vol. 15, No. s4.
Traore et al., "Flexible Synthesis and Evaluation of Diverse Anti-Apicomplexa Cyclic Peptides", J. Org. Chem. 2013, 78, pp. 3655-3675.

* cited by examiner

*Primary Examiner* — Karlheinz R Skowronek
*Assistant Examiner* — Catherine Mader
(74) *Attorney, Agent, or Firm* — Cantor Colburn LLP

(57) ABSTRACT

The present invention relates to a method for preparing a cyclic peptide with antiparasite activity and anticancer activity. The invention also relates to this peptide as an antiparasite agent, for example in the treatment of toxoplasmosis and as an anticancer agent. The invention also relates to the use of this cyclic peptide for treating organs ex vivo before transplantation.

17 Claims, No Drawings

CYCLIC PEPTIDES WITH AN ANTI-PARASITIC ACTIVITY

TECHNICAL FIELD

The field of the present invention is that of the preparation of a cyclic peptide with antiparasite activity. The invention also relates to this peptide as an antiparasite agent, for example in the treatment of toxoplasmosis. The invention also relates to the use of this cyclic peptide for treating organs ex vivo before transplantation.

BACKGROUND

Toxoplasmosis is a parasitic disease, the agent of which is an opportunistic intracellular protozoan, *Toxoplasma gondii*. Clinical signs of the disease in immunocompetent persons are rare. However, toxoplasmosis is increasingly associated in these persons with lymphadenopathies, fevers, neurological signs (decrease in the intelligence quotient, reduction of psychomotor performances), ocular lesions, severe disseminated infections and even neurological or psychiatric lesions such as schizophrenia. In immunodepressed patients (for example AIDS, grafted, patients having haematological problems) or in the fetus, *Toxoplasma gondii* appears as an opportunistic pathogen which may cause severe lesions.

During its parasitic cycle, *Toxoplasma gondii* may appear in three different forms: a tachyzoite form, a bradyzoite form and an oocyte form. The chronic form of the disease is due to the bradyzoite form, contained in intracellular cysts (5 to 70 μm) notably localized in nerve and muscle cells. The cysts persist in these tissues until death of the host. The host-parasite immune equilibrium allows them to be kept quiescent. These forms are very resistant and may survive several days at room temperature.

A certain number of molecules (for example pyrimethamine, sulfadiazine and sulfadoxine) are present on the market. However, these molecules have an effect against the tachyzoite primary form of the disease. Indeed, presently there is no treatment against chronic toxoplasmosis, no drug to this day being capable of removing the tissue cysts. The only known molecule has a cysticidal effect in vitro is atovaquone (U.S. Pat. No. 5,641,769), the cysticidal activity of this molecule in vivo having never been demonstrated.

*Toxoplasma gondii* belongs to the phylum of Apicomplexes (branch Apicomplexa) which groups a large number of parasites responsible for diseases such as malaria, neosporosis, coccidiosis and cryptosporidiosis. With research work aiming at identifying new anti-parasite active ingredients, it was possible to identify apicidin, acyclic tetrapeptide extracted from the fungus *Fusarium pallidoroseum*. Apicidine has some effectiveness in vivo on mice infected by the malaria of *Plasmodium berghei* (Darkin-Rattray et al. Proc. Natl. Acad. Sci. USA 1996; Singh et al., Tetrahedron Lett. 1996). This molecule would have an inhibitory action on histone deacetylase (HDAC) of *Plasmodium berghei*.

There exist different forms of HDAC. The inhibitors of HDAC represent a class of more than 8,000 compounds. Today, they are the subject of research and development, for example as anticancer agents or as effective and selective immunosuppressive agents in humans. The class of the HDAC inhibitors notably comprises cyclic natural derivatives of the peptide type having shown some effectiveness. Among the latter, mention may be made of chlamydocin, isolated from the fungus *Diheterospora chlamydosporia* and which has demonstrated an anticancer activity in vitro, and derivatives of chlamydocin, isolated from the fungus *Peniophora* sp. and which cause interruption of the cell cycle in plants (Tani et al. Phytochem. 2003).

A certain number of drawbacks are associated with the use of the compounds with a human therapeutic target, which are derived from biological material such as notably apicidin and chlamydocin. Notably, it is impossible to control the exact composition of the extract, for example the presence of associated molecules potentially having an uncontrolled biological effect. Further, the problem is posed of the accessibility of said material. The problem of the cost for preparing the active compound is also posed.

Nishino et al. (Nishino et al., Bioorg. Med. Chem, 2004) propose several chemical syntheses of derivatives of chlamydocin. Each synthesis involves several reactions. In order to obtain a derivative, each synthesis applies a different synthesis approach, so that the proposed syntheses do not have much flexibility.

BRIEF SUMMARY

The invention proposes a chemical synthesis method aiming at providing compounds for which purity is under control.

The invention further proposes an easy preparation method to apply starting from easily accessible intermediates and using common products.

The invention also proposes a method having an attractive production cost.

The invention additionally proposes an active HDAC inhibitor in parasites and having no or little activity in humans, as well as a method for synthesizing such an inhibitor.

The invention further proposes a synthesis method, the starting compound of which is a synthesis intermediate.

The inventors were therefore interested in a novel method for preparing a cyclic tetrapeptide with antiparasite activity.

DETAILED DESCRIPTION

Method

The invention therefore relates to a method for preparing a cyclic peptide of formula (I):

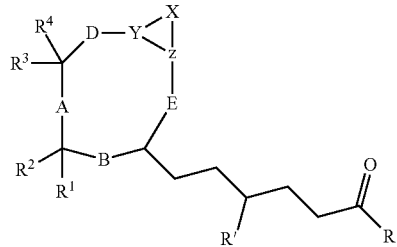

characterized in that an intermediate compound of formula (II) is reacted:

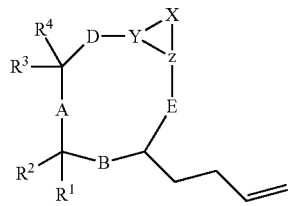

with a carbonyl xanthate of formula (III):

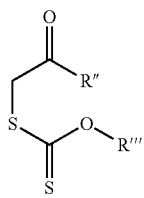

and in that, optionally in a second step, it is proceeded with the de-protection of the obtained compound.

The groups of the compounds of formulae (I) and (II) have the following meaning:

Y and Z, either identical or different, represent a carbon or nitrogen atom, Y and Z being optionally connected together through a double bond, X represents 3 or 4 carbon, nitrogen and/or oxygen atoms optionally substituted, A represents a group $R^5_a$—(N—CO)$_b$—$R^6_c$ B represents a group $R^7_d$—(N—CO)$_e$—$R^8_f$ D represents a group $R^9_g$—(N—CO)$_h$—$R^{10}_i$ or $R^9_g$—(CO)$_h$—$R^{10}_i$ E represents a group $R^{11}_j$—(N—CO)$_k$—$R^{12}_l$ wherein $R^5, R^6, R^7, R^8, R^9, R^{10}, R^{11}, R^{12}$, either identical or different, represent one or two or three carbon, nitrogen or oxygen atoms, wherein a, b, c, d, e, f, g, h, i, j, k and l, either identical or different, are selected from 0, 1, 2 or 3, provided that the number of atoms of the ring is comprised between 12 and 16.

R represents H; OH; SH; an amine group; an alkyl, haloalkyl or heteroalkyl group containing between 1 and 10 carbon atoms as a linear or branched chain; an alkenyl or alkynyl group containing between 2 and 10 carbon atoms as a linear or branched chain; one or more cycloalkyl, cycloalkenyl or cycloalkynyl groups containing between 3 and 10 carbon atoms as a linear or branched chain; one or more aryl or heteroaryl groups containing between 3 and 10 carbon atoms per ring; an alkaryl or aralkyl group containing between 1 and 10 carbon atoms, the terms aryl and alkyl having the definitions above; an alkoxy, thioalkyl, sulfonylalkyl, aminoalkyl groups containing between 1 and 10 carbon atoms as a linear or branched chain; an alkoxyalkyl, alkylthioalkyl, alkylsulfonylalkyl, alkylaminoalkyl group containing between 1 and 30 carbon atoms as a linear or branched chain; one or more heterocyclic groups containing between 5 and 10 carbon atoms per ring;

R' represents H or a xanthate group;

$R^1, R^2, R^3$ and $R^4$, either identical or different, represent H; OH, SH; an amine group; an alkyl, haloalkyl or heteroalkyl group containing between 1 and 30 carbon atoms as a linear or branched chain; an alkenyl or alkynyl group containing between 2 and 30 carbon atoms as a linear or branched chain; one or more cycloalkyl, cycloalknyl or cycloalkynyl groups containing between 3 to 30 carbon atoms as a linear or branched chain; one or more aryl or heteroaryl groups containing between 3 to 10 carbon atoms per ring; an alkaryl or aralkyl group containing between 1 and 30 carbon atoms, the terms aryl and alkyl having the definitions above; an alkoxy, thioalkyl, sulfonylalkyl, aminoalkyl group containing between 1 and 30 carbon atoms as a linear or branched chain; an alkoxyalkyl, alkylthioalkyl, alkylsulfonylalkyl, alkylaminoalkyl group containing between 1 and 30 carbon atoms as a linear or branched chain; one or more heterocyclic groups containing between 5 and 10 atoms per cycle, either saturated or unsaturated, comprising at least one heteroatom selected from N, O and S, said heterocyclic group(s) may be substituted, and directly or indirectly bound by a bivalent alkylene radical to the ring of said peptide.

The groups of the compound of formula (III) has the following meaning:

R" represents H; an amine group; an alkyl, haloalkyl or heteroalkyl group containing between 1 and 10 carbon atoms as a linear or branched chain; an alkenyl or alkynyl group containing between 2 and 10 carbon atoms as a linear or branched chain; one or more cycloalkyl, cycloalkenyl or cycloalkynyl groups containing between 3 to 10 carbon atoms as a linear or branched chain; one or more aryl or heteroaryl groups containing between 3 to 10 carbon atoms per ring; an alkaryl or aralkyl group containing between 1 and 10 carbon atoms, the aryl and alkyl terms having the definitions above; an alkoxy, thioalkyl, sulfonylalkyl, aminoalkyl group containing between 1 and 10 carbon atoms as a linear or branched chain; an alkoxyalkyl, alkylthioalkyl, alkylsulfonylalkyl, alkylaminoalkyl group containing between 1 and 10 carbon atoms as a linear or branched chain; one or more heterocyclic groups containing between 5 and 10 carbon atoms per ring;

R''' represents H; an alkyl or haloalkyl group containing between 1 and 10 carbon atoms as a linear or branched chain.

According to the invention, the term "alkyl" designates a linear or branched hydrocarbon radical with 1 to 30 carbon atoms, such as, as an indication, a methyl, ethyl, propyl, isopropyl, butyl, tert-butyl, isobutyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl radical. The alkyl group defined above may include one or more halogen atoms (fluorine, chlorine, bromine or iodine). In this case, one refers to a "haloalkyl" group. The alkyl group may further comprise hetero-atoms selected from P, O, N, S and Se. In this case one refers to a "hetero-alkyl" group.

By "alkenyl", is meant a linear or branched hydrocarbon chain with 2 to 30 carbon atoms comprising one or more double bonds. Examples of alkenyl groups are the alkenyl groups bearing a single double bond such as —CH—CH=CH—$CH_2$, $H_2C$=CH-(vinyl) or $H_2C$=CH—$CH_2$-(allyl).

By "alkenyl", is meant a linear or branched hydrocarbon chain with 2 to 30 carbon atoms comprising one or more triple bonds. Examples of alkenyl groups are the alkenyl groups bearing a single triple bond such as —$CH_2$—C≡CH.

The term of "cycloalkyl" designates saturated hydrocarbon groups which may be mono or polycyclic and comprise from 3 to 10 carbon atoms. These are for example monocyclic cycloalkyl groups such as cyclopropyl, cyclobutyl, cyclopentyl, cyclohexyl, cycloheptyl, cyclooctyl, cyclononyl, cyclodecyl, cycloundecyl and cyclododecyl.

By "cycloalkenyl", is meant according to the invention a group derived from a cycloalkyl group as defined above, having one or more double bonds, for example two double bonds. This is for example the cyclohexene group (one double bond) or cyclopenta-1,3-diene (two double bonds).

By "cycloalkenyl" is meant according to the invention a group derived from a cycloalkyl group as defined above, having one or more triple bonds, for example one triple bond.

The term of "aryl" represents an aromatic monocyclic or polycyclic hydrocarbon group comprising 3 to 10 carbon atoms per ring, such as phenyl or naphthyl.

The term of "heteroaryl" designates a monocyclic or polycyclic aromatic group comprising between 3 and 10 carbon atoms per cycle and comprising 1, 2 or 3 endocyclic heteroatoms per ring selected from P, O, N, S and Se. Examples thereof are furyl, thienyl, pyrrolyl, oxazolyl, isoxazolyl, thiazolyl, isothiazolyl, imidazolyl, pyrazolyl, oxadiazolyl, triazolyl, thiadiazolyl, pyridyl, pyridazinyl, pyrazinyl and triazinyl groups.

By "alkaryl", is meant an alkyl group substituted with an aryl group, both of these groups being defined above.

By "aralkyl", is meant an alkyl group, substituted with an aryl group, both of these groups being defined above.

By "alkoxy", is meant an O-alkyl group having 1 to 30 carbon atoms, notably a methoxy, ethoxy, propoxy and butoxy group.

By "alkoxyalkyl", is meant an alkyl-O-alkyl group having from 1 to 30 carbon atoms. The "thioalkyl" or "alkylthioalkyl", "sulfonylalkyl" or "alkylsulfonylalkyl" and "aminoalkyl" or "alkylaminoalkyl" groups further include one or more sulphur atoms, one or more sulfonyl groups and one or more amine functions, respectively.

The term of "hetero-cyclic group" designates monocyclic or polycyclic saturated or unsaturated carbon rings, having 1, 2 or 3 endocyclic hetero-atoms selected from P, O, N, S and Se. These are generally derivatives of the hetero-aryl groups described above. Examples of unsaturated hetero-cycles are dihydrofuryl, dihydrothienyl, dihydropyrrolyl, pyrrolinyl, oxazolinyl, thiazolinyl, imidazolinyl, pyrazolinyl, isoxazolinyl, isothiazolinyl, oxadiazolinyl, pyranyl and mono-unsaturated derivatives of piperidine, dioxane, piperazine, trithiane, morpholine, dithiane, thiomorpholine, as well as tetrahydropyridazinyl, tetrahydropyrimidinyl, and tetrahydrotriazinyl.

The groups defined above may according to the invention be substituted with one or more nitro-, cyano-, hydroxy, carboxy, carbonyl or amino groups, with one or more halogens or with one or more nitrile, cyanhydrin, aldehyde functions.

According to an embodiment of the invention, the group R of the compound of formula (I) represents H; OH; SH; an alkyl or haloalkyl group containing between 1 and 10 carbon atoms as a linear or branched chain; one or more aryl or hetero-aryl groups containing between 3 and 10 carbon atoms per ring; an alkoxy, thioalkyl, sulfonylalkyl, aminoalkyl group containing between 1 and 10 carbon atoms as a linear or branched chain; one or more hetero-cyclic groups containing between 5 and 10 carbon atoms per ring.

According to another embodiment of the invention, the group R of the compound of formula (I) is selected from $CH_2Cl$, $CH_2Br$, $CF_3$, OH, O—$CH_2$—$C_6H_6$, NHOH, $CH_2$—S—CS—O—$CH_2CH_3$, $CH_2CH_3$, CO—$CH_2CO_2$—$CH_2CH_3$, CHOH—$CH_3$, CH(OTBDMS)$CH_3$.

According to another embodiment of the invention, the group R' of the compound of formula (I) represents H.

According to an embodiment of the invention, the group R" of the compound of formula (III) represents H; an alkyl or haloalkyl group containing between 1 and 10 carbon atoms as a linear or branched chain; one or more aryl or hetero-aryl groups containing between 3 to 10 carbon atoms per ring; an alkoxy, thioalkyl, sulfonylalkyl, aminoalkyl group containing between 1 and 10 carbon atoms as a linear or branched chain; one or more hetero-cyclic groups containing between 5 and 10 carbon atoms per ring.

According to an embodiment of the invention, the group R" of the compound of formula (III) is selected from $CH_2Cl$, $CH_2Br$, $CF_3$, O—$CH_2$—$C_6H_6$, $CH_2CH_3$, COCH$_2$CO$_2$Et, CH(OTBDMS)$CH_3$.

In an embodiment of the invention, b=1; e=1; h=0 and k=1.

According to this method, it is thereby possible to obtain a cyclic peptide of formula (IV):

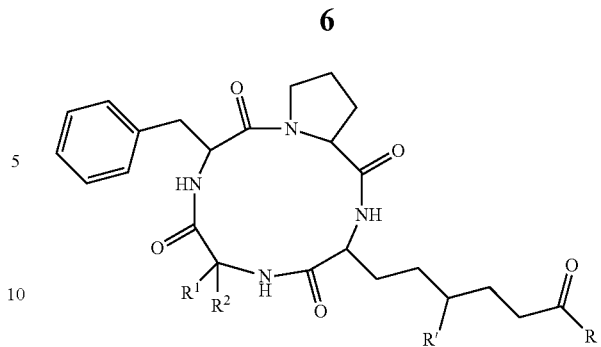

wherein R, R', $R^1$ et $R^2$ are as defined above,

By a method according to which an intermediate compound of formula (V):

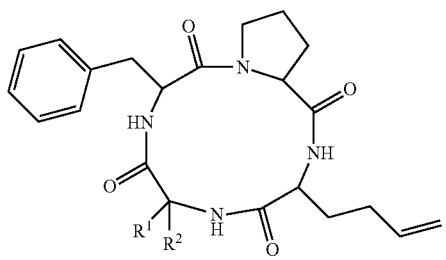

is reactive with a carbonyl xanthate of formula (III):

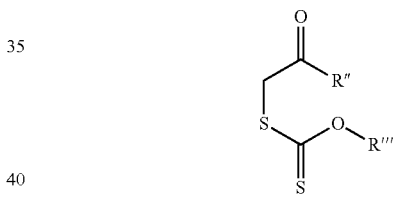

wherein R" and R'" are as defined above, and in that, optionally in a second step, it is proceeded with deprotection of the obtained compound.

An example of a cyclic peptide according to the invention is the compound of formula (IV'f):

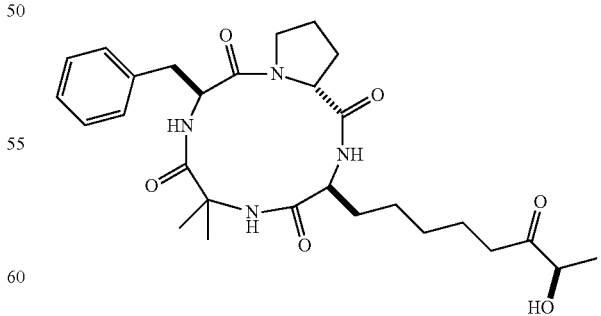

The present invention also relates to an intermediate compound of formula (II), (V) wherein X, Y, Z, A, B, D, E, $R^1$, $R^2$, $R^3$ and $R^4$ are as defined earlier, but also of formula (VI) or (VII), both of the latter compounds being illustrated below:

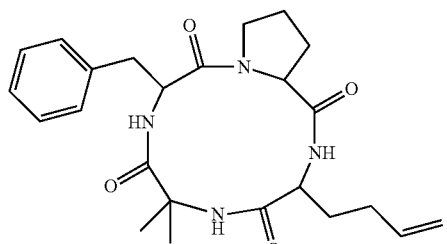

(VI)

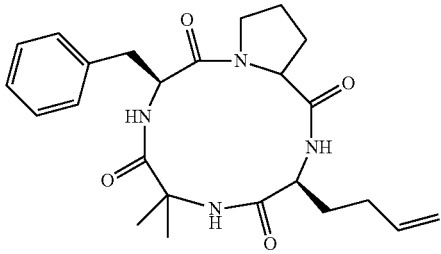

(VII)

A preferred intermediate compound according to the invention fits the formula (V) wherein at least one of $R^1$ and $R^2$ represents $CH_2C\equiv CH$. When only one of $R^1$ and $R^2$ represents $CH_2C\equiv CH$, the other one advantageously represents H.

Cyclic Peptides with Anti-Parasitic Activity

The invention also relates to a cyclic peptide with anti-parasitic activity of formula (I):

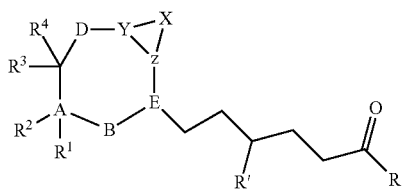

wherein X, Y, Z, A, B, D, E, R, R', $R^1$, $R^2$, $R^3$ and $R^4$ are as defined above.

An example of a cyclic peptide which may be obtained according to the present invention is the one illustrated by the formula (IV):

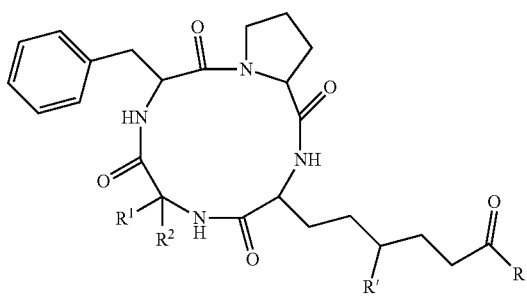

wherein R, R', $R^1$ and $R^2$ are as defined above.

Another example of a cyclic peptide which may be obtained according to the present invention is the one illustrated by formula (IV):

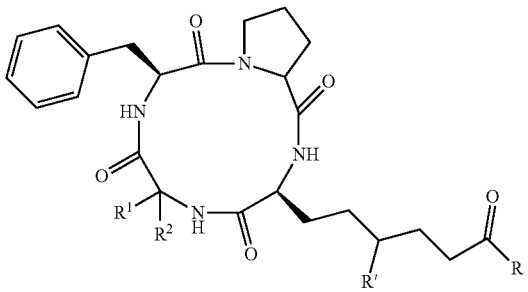

wherein R, R', $R^1$ and $R^2$ are as defined above.

According to an embodiment, R' represents H and/or $R^1$ and $R^2$ represent $CH_3$.

According to another embodiment either combined or not to the aforementioned embodiments, at least one of $R^1$ and $R^2$ represents $CH_2C\equiv CH$, the other of $R^1$ and $R^2$ representing H, if necessary.

According to still another embodiment, either combined or not to the aforementioned embodiments, one of $R^1$ and $R^2$ represents a heterocycle with 5 atoms selected from C, N and O, said heterocycle being bound by a methylene radical to the ring of said peptide. In this embodiment, one of the heteroatoms is substituted with a group selected from amino acids and peptides.

According to another embodiment, either combined or not to the aforementioned embodiments, R represents CHOH—$CH_3$.

According to an embodiment of the invention, the cyclic peptide with anti-parasitic activity is the compound of formula (IV'f):

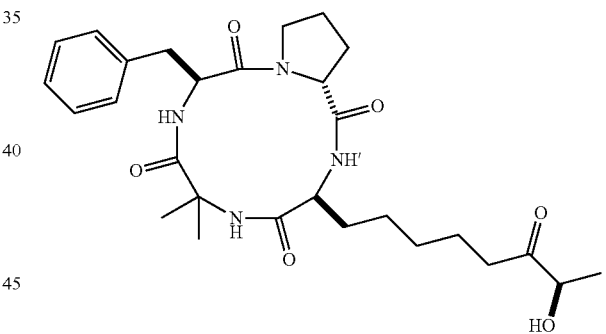

According to another embodiment, the invention relates to a cyclic peptide having an effect against toxoplasmosis, for example against the chronic form of toxoplasmosis.

Uses

The invention provides a pharmaceutical composition comprising a cyclic peptide of the invention as defined earlier, and notably the peptides of formula (IV), for example those more specifically discussed and/or illustrated above. The cyclic peptide is the, or at least one of the active ingredients of said composition.

A pharmaceutical composition of the invention is intended for an antiparasite treatment, notably treatment of malaria, toxoplasmosis, coccidiosis, cryptosporidiosis or neosporosis.

The invention also relates to a cyclic peptide of formula (I) or (IV) for its use in the treatment of malaria, toxoplasmosis, coccidiosis, cryptosporidiosis or neosporosis.

The invention also relates to the use of the cyclic peptide of formula (I) or (IV) for preparing a drug for treatment of an infection by a parasite, and notably for treating malaria, toxoplasmosis, coccidiosis, cryptosporidiosis or neosporosis.

The invention also relates to a cyclic peptide of the invention for an anti-cancer treatment, and also to the use of such a peptide for making a drug intended to treat a cancer. Thus, an anti-cancer pharmaceutical composition comprising a peptide of the invention is also provided. The analogy of the peptides of the invention with cyclic natural derivatives of the peptide type known for their anti-cancer activity, gives the possibility of contemplating identical properties for the peptides of the invention. In the part of the examples which follows, these properties are moreover demonstrated for a preferred compound of the invention.

The invention also relates to the use of the cyclic peptide of formula (I) or (IV) for treating an organ ex vivo before transplantation.

Finally, the invention relates to a method for treating an infection by a parasite, and notably malaria, toxoplasmosis, coccidiosis, cryptosporidiosis or neosporosis, as well as a method for treating a cancer, these methods applying at least one cyclic peptide of the invention as defined above.

EXAMPLES

1. Preparation of the Intermediate Compound of Formula (VI), Notably the Compound (VII)

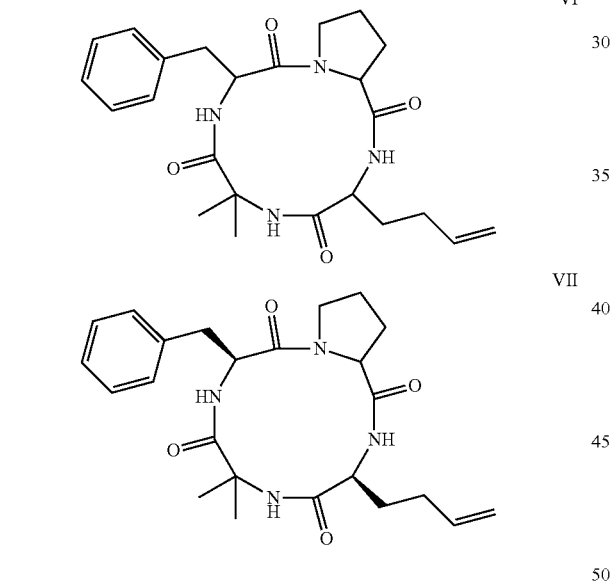

The intermediate compound (VI) was obtained according to the method described below.

Scheme 1

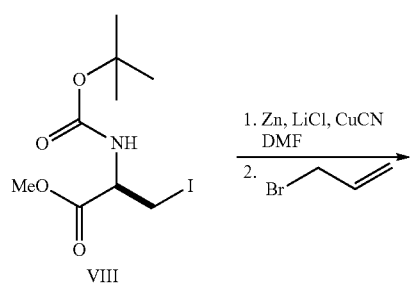

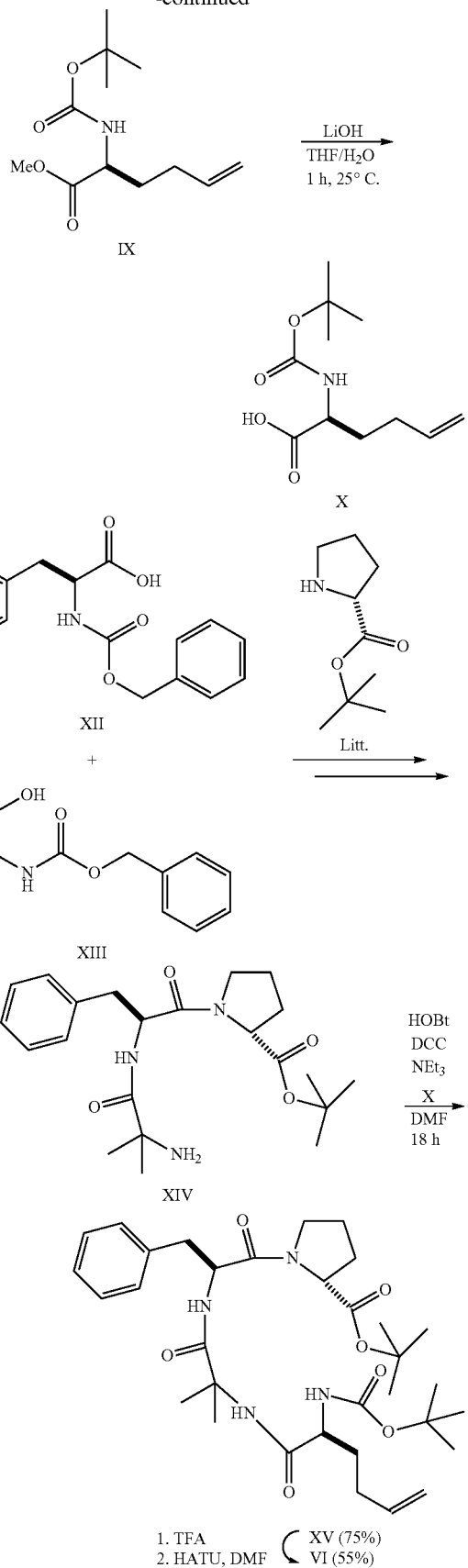

Briefly, an amino acid (X) was synthesized from (VIII) (Jackson et al., Org. Synth. 2005) according to the method described by Kiyota et al., (Shimasaki et al., Tetrahedron 2006). The tripeptide (XIV) is obtained from the three commercial amino acids (XI), (XII) and (XIII) according to a peptide synthesis in the liquid phase (Bhuiyan et al., Bioorg. Med. Chem. 2006). The compound (XIV) reacts with the compound (X) giving the tetrapeptide (XV), which leads to the intermediate compound (VII).

Preparation of the compound (S)-methyl 2-(tert-butoxycarbonylamino)hex-5-enoate (IX)

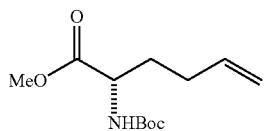 [SMILES: C=CCC[C@H](NC(=O)OC(C)(C)C)C(=O)OC]

In an anhydrous DMF solution (28 mL) containing zinc powder (2.48 g, 37.9 mmol) 1,2-dibromoethane (0.17 mL) is injected under argon. The solution is stirred for 20 min at room temperature. TMSCl (50 μL) is injected and the solution is heated with stirring to 60° C. for 30 min. (R)-methyl 2-(tert-butoxycarbonylamino)-3-iodopropanoate (VIII) (2.0 g, 6.08 mmol) in DMF (8 mL) is added drop wise. The solution is then stirred for 20 min at 60° C. LiCl (587 mg, 13.8 mmol) and CuCN (619 mg, 6.9 mmol) in DMF (6.5 mL) are injected at −55° C. and the solution is placed at 0° C. for 10 min. The latter is again placed at −55° C. and allyl bromide (1.05 mL, 12 mmol) is injected. After 5 min, the solution is placed at 0° C. and stirred for 2 hours at this temperature. The zinc which has not reacted is removed by filtration on celite and the filtrate is treated with a saturated $NH_4Cl$ solution. The product is extracted with ethyl acetate (EtOAc). The collected organic phases are washed with a saturated NaCl solution, and then dried on $MgSO_4$ and evaporated. After flash chromatography (silica gel, 8% EtOAc/cyclohexane), the product (IX) (1.38 g, 93%) is isolated as a colorless oil.

$R_f$=0.25 (10% EtOAc/cyclohexane); $[\alpha]^D$=+20.5 (c=1, $CHCl_3$); IR $\nu_{max}$ (film, $CH_2Cl_2$) 3358, 2978, 1745, 1716, 1518, 1453, 1366, 1249, 1163, 914 cm$^{-1}$; $^1$H NMR (400 MHz, $CDCl_3$) δ ppm 1.45 (s, 9H), 1.74 (m, 1H), 1.90 (m, 1H), 2.12 (m, 2H), 3.74 (s, 3H), 4.32 (m, 1H), 5.00 (bd, J=10.3 Hz, 1H), 5.05 (bd, J=17.0, 1H), 5.18 (bd, J=7.2 Hz, NH), 5.79 (m, 1H); $^{13}$C NMR (100 MHz, $CDCl_3$) δ ppm 28.4 (3×$CH_3$), 29.6 ($CH_2$), 32.0 ($CH_2$), 52.3 ($CH_3$), 53.0 (CH), 79.8 (C), 115.7 ($CH_2$), 137.0 (CH), 155.4 (C), 173.4 (C); Mass (ESI+) m/z (%) 266 (100) [M+Na]$^+$, 210 (43), 166 (38).

Preparation of acid (s)-2-(tert-butoxycarbonylamino) hex-5-enoic acid (X)

In a solution of $THF/H_2O$ (1:1, 35 mL) containing the product (IX) (1 g, 4.1 mmol) $LiOH.H_2O$ (432 mg, 10.3 mmol) is added in one portion. The mixture is stirred for 1 h at room temperature. The solvent is then evaporated and then a 5% $H_3PO_4$ solution in water is added until a pH=3 is obtained. The product is then extracted with EtOAc, dried ($MgSO_4$), and then evaporated. After purification, the product (X) (840 mg, 89%) is isolated as a colorless lacquer.

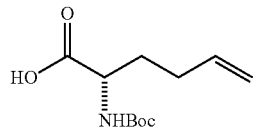 [SMILES: C=CCC[C@H](NC(=O)OC(C)(C)C)C(=O)O]

Preparation of (3S,9S,14aR)-9-benzyl-3-(but-3-enyl)-6,6-dimethyl decahydropyrrolo[1,2-a][1,4,7,10]tetraazacyclododecine-1,4,7,10-tetraone (VII)

To a solution of tripeptide H-Aib-L-Phe-D-Pro-Ot-Bu (XIV) (1.38 g, 3.42 mmol) and of methyl (S)-2-(benzyloxycarbonylamino)-5-hexenoate (X) (784 mg, 3.42 mmol) in anhydrous DMF (7 mL) are added $HOBt.H_2O$ (525 mg, 3.45 mmol), DCC (850 mg, 4.12 mmol) and triethyl amine (0.5 mL) under argon. The solution is stirred at room temperature for 18 h. The DMF is evaporated and the residue is diluted in EtOAc. This phase is washed with a 10% citric acid aqueous solution, a 4% sodium carbonate aqueous solution and a saturated NaCl aqueous solution. The organic phase is dried ($MgSO_4$) and evaporated. After flash chromatography (silica gel, 1.5% $MeOH/CH_2Cl_2$), the tetrapeptide (XV) (1.58 g, 75%) is obtained as a colorless lacquer. $R_f$=0.09 (2% MeOH/$CH_2Cl_2$); LRMS (ESI+) m/z (%) 637 (100) [M+Na]$^+$, 615 (20) [M+H]$^+$; HRMS (ESI+): m/z calculated for $C_{33}H_{50}N_4O_7Na$, 637.3577. found 637.3567. The tetrapeptide (XV) (1.57 g, 2.55 mmol) is dissolved in trifluoroacetic acid (7 mL) at 0° C. and the solution is stirred for 3 h at this temperature. After evaporation, the product is precipitated from dry ether in order to obtain after filtration a de-protected salt (1.08 g, 74%). The latter (900 mg, 1.57 mmol) is taken up in anhydrous DMF (140 mL). HATU (666 mg, 1.75 mmol) and diisopropyl ethyl amine (0.81 mL) are added in five portions over an interval of 30 min under strong stirring. The stirring is continued for 1 h at room temperature. The DMF is evaporated and EtOAc is added. After washing with a 10% citric acid aqueous solution, followed by a 4% sodium carbonate aqueous solution, the organic phase is dried ($MgSO_4$) and evaporated. After flash chromatography (silica gel, 1% $MeOH/CH_2Cl_2$), the cyclotetrapeptide (VII) (512 mg, 74%) is isolated as a white solid.

$R_f$=0.17 (40% EtOAc/cyclohexane); $[\alpha]^D$=−110 (c=0.84, $CHCl_3$); IR $\nu_{max}$ (thin film, $CH_2Cl_2$) 3303, 2930, 1678, 1663, 1630, 1663, 1529, 1427, 1251, 1181, 913 cm$^{-1}$; $^1$H NMR (400 MHz, $CDCl_3$) δ ppm 1.31 (s, 3H), 1.67-1.82 (m, 6H), 1.92 (m, 1H), 2.09 (m, 2H), 2.16 (m, 1H), 2.30 (m, 1H), 2.94 (dd, J=13.5, 5.8 Hz, 1H), 3.19-3.28 (m, 2H), 3.86 (m, 1H), 4.30 (ddd, J=10.1, 7.5, 7.5 Hz, 1H), 4.66 (m, 1H), 4.97 (m, 1H), 5.00 (m, 1H), 5.17 (ddd, J=10.1, 10.0, 5.8 Hz, 1H), 5.78 (ddt, J=16.8, 10.2, 6.6 Hz, 1H), 6.18 (s, NH), 7.16-7.28 (m, 5H, NH), 7.61 (d, J=10.1 Hz, NH); $^{13}$C NMR (100 MHz, $CDCl_3$) δ ppm 23.4 ($CH_3$), 24.6 ($CH_2$), 24.8 ($CH_2$), 26.3 ($CH_3$), 28.2 ($CH_2$), 29.6 ($CH_2$), 35.7 ($CH_2$), 46.7 ($CH_2$), 53.2 (CH), 53.7 (CH), 57.6 (CH), 58.5 (C), 115.5 ($CH_2$), 126.5 (CH), 128.4 (2×CH), 128.9 (2×CH), 136.9 (C, CH), 171.5 (C), 172.6 (C), 174.2 (C), 175.4 (C); Mass (ESI+) m/z (%) 463 (100) [M+Na]$^+$; HRMS (ESI+): m/z calculated for $C_{24}H_{32}N_4O_4Na$, 463.2321. found 463.2316.

2. Preparation of Carbonyl Xanthates of Formula (III)

As this is illustrated in the scheme 2 below, the products (XVI$_{a-g}$) react with potassium ethyl xanthate, giving the carbonyl Xanthates (III$_{a-g}$).

Scheme 2

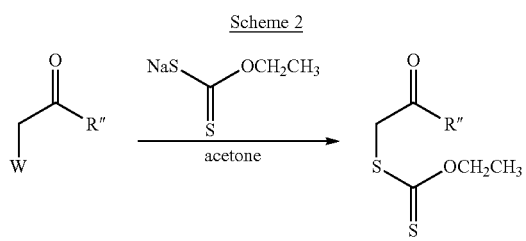

XVIa: W=Cl; R"=CH₂Cl    IIIa: R"=CH₂Cl (Litt)
XVIb: W=Br; R"=CF₃    IIIb: R"=CF₃ (Litt)
XVIc: W=Cl; R"=OBn    IIIc: R"=OBn (68%; purified by distillation)
XVId: W=Br; R"=CH₂CH₃    IIId: R"=CH₂CH₃ (63%; purified by distillation)
XVIe: W=Cl; R"=COCH₂COEt    IIIe: R"=COCH₂COEt (67%; purified by distillation)
XVIf: W=Cl; R"=CH(OTBDMS)CH₃ (Configuration S)
    IIIf: R"=CH₂Cl (96%; purified by chromatography)
XVIf: W=Cl; R"=CH(OTBDMS)CH₃ (Configuration R)
    IIIg: R"=CH₂Cl (96%; purified by chromatography)

Typical procedure for preparing intermediate compound (III), example with benzyl 2-(ethoxycarbonothioylthio)acetate (IIIc)

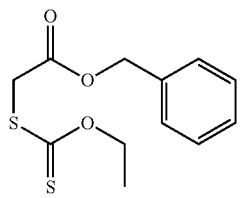 [SMILES: CCOC(=S)SCC(=O)OCc1ccccc1]

To a solution of benzyl 2-chloroacetate 1c (2.76 g, 15 mmol) in acetone (50 mL) is added at 0° C. a solution of potassium ethyl xanthate (2.6 g, 16 mmol) in acetone (50 mL). The solution is stirred for 4 h at room temperature. The acetone is evaporated and CH₂Cl₂ is added. The organic phase is washed with a saturated NaCl solution. The organic phase is dried (MgSO₄) and evaporated. The product is distilled with a Kugelrohr (13 mbars, 180-200° C.) in order to obtain (IIIc) (2.74 g, 68%) as a pale yellow oil. In the case of (IIIf) and (IIIg), conventional chromatography is carried out.
$R_f$=0.21 (5% EtOAc/cyclohexane); IR $v_{max}$ (film) 2982, 1740, 1615, 1498, 1455, 1376, 1232, 1150 cm⁻¹; ¹H NMR (400 MHz, CDCl₃) δ ppm 1.35 (t, J=7.1 Hz, 3H), 3.93 (s, 2H), 4.58 (q, J=7.1 Hz, 2H), 5.18 (s, 2H), 7.32-7.36 (m, 5H). ¹³C NMR (100 MHz, CDCl₃) δ ppm 13.7 (CH₃), 37.9 (CH₂), 67.6 (CH₂), 70.7 (CH₂), 128.3 (CH), 128.4 (2×CH), 128.6 (2×CH), 135.3 (C), 167.8 (C), 212.4 (C); Mass (ESI+) m/z (%) 293 (100) [M+Na]⁺.

Preparation of O-ethyl S-2-oxobutyl carbonodithioate (IIId)

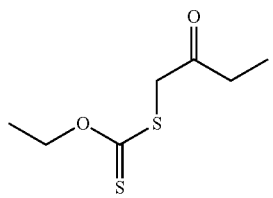

Product (IIId), purified by distillation (Kugelrohr, 2.2 mbars, 100° C.), % yield=63% (pale yellow oil); IR $v_{max}$ (film) 2980, 1729, 1717, 1457, 1376, 1224, 1113, 1052 cm⁻¹; ¹H NMR (400 MHz, CDCl₃) δ ppm 1.11 (t, J=7.1 Hz, 3H), 1.42 (t, J=7.1 Hz, 3H), 2.65 (q, J=7.1 Hz, 2H), 4.00 (s, 2H), 4.63 (q, J=7.1 Hz, 2H); ¹³C NMR (100 MHz, CDCl₃) δ ppm 7.97 (CH₃), 13.9 (CH₃), 35.4 (CH₂), 45.3 (CH₂), 71.0 (CH₂), 204.1 (C), 213.6 (C); Mass (ESI+) m/z (%) 215 (100) [M+Na]⁺.

Preparation of ethyl 4-(ethoxycarbonothioylthio)-3-oxobutanoate (IIIe)

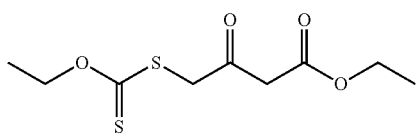

Product (IIIe), purified by distillation (Kugelrohr, 2.2 mbars, 150° C.), % yield=67% (pale yellow oil); IR $v_{max}$ (film) 2983, 1745, 1616, 1376, 1225, 1113, 1048 cm⁻¹; ¹H NMR (400 MHz, CDCl₃) δ ppm 1.30 (t, J=7.1 Hz, 3H), 1.42 (t, J=7.1 Hz, 3H), 3.65 (s, 2H), 4.12 (s, 2H), 4.20 (q, J=7.1 Hz, 2H), 4.64 (q, J=7.1 Hz, 2H); ¹³C NMR (100 MHz, CDCl₃) δ ppm 13.8 (CH₃), 14.2 (CH₃), 45.5 (CH₂), 48.3 (CH₂), 61.8 (CH₂), 71.2 (CH₂), 166.9 (C), 196.3 (C), 213.0 (C); Mass (ESI+) m/z (%) 273 (100) [M+Na]⁺.

Preparation of (R)—S-3-(tert-butyldimethylsilyloxy)-2-oxobutyl O-éthyl carbonodithioate (IIIf)

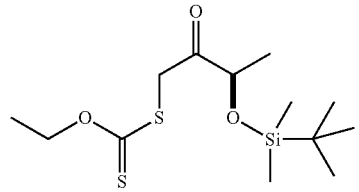 [SMILES: CCOC(=S)SCC(=O)[C@@H](C)O[Si](C)(C)C(C)(C)C]

Product (IIIf), purified by flash chromatography (5% ether/cyclohexane), % yield=96% (pale yellow oil); $R_f$=0.25 (4% ether/cyclohexane); [α]$^D$=−7.3 (c=1.15, CHCl₃); IR $v_{max}$ (film) 2955, 2931, 1735, 1728, 1363, 1224, 1112, 1051, 836 cm⁻¹; ¹H NMR (400 MHz, CDCl₃) δ ppm 0.13 (s, 3H), 0.14 (s, 3H), 0.95 (s, 9H), 1.37 (d, J=6.8 Hz, 3H), 1.41 (t, J=7.1 Hz, 3H), 4.28 (d, J=17.9 Hz, 1H), 4.35 (d, J=17.9 Hz, 1H), 4.62 (q, J=7.1 Hz, 2H); ¹³C NMR (100 MHz, CDCl₃) δ ppm −4.9 (CH₃), −4.4 (CH₃), 13.9 (CH₃), 18.1 (C), 21.0 (CH₃), 25.9 (2×CH₃), 42.8 (CH₂), 70.6 (CH₂), 75.0 (CH), 205.7 (C), 213.6 (C); Mass (ESI+) m/z (%) 345 (100) [M+Na]⁺, 323 (5).

Preparation of (S)—S-3-(tert-butyldimethylsilyloxy)-2-oxobutyl O-ethyl carbonodithioate (IIIg)

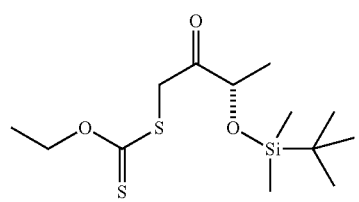 [SMILES: CCOC(=S)SCC(=O)[C@H](C)O[Si](C)(C)C(C)(C)C]

Product (IIIg), purified by flash chromatography (5% ether/cyclohexane), % yield=94% (pale yellow oil); $R_f$=0.25 (4% ether/cyclohexane); $[\alpha]^D$=+7.4 (c=1.2, $CHCl_3$); IR $v_{max}$ (film) 2955, 2931, 1735, 1728, 1363, 1224, 1112, 1051, 836 cm$^{-1}$; $^1$H NMR (400 MHz, $CDCl_3$) δ ppm 0.13 (s, 3H), 0.14 (s, 3H), 0.95 (s, 9H), 1.37 (d, J=6.8 Hz, 3H), 1.41 (t, J=7.1 Hz, 3H), 4.28 (d, J=17.9 Hz, 1H), 4.35 (d, J=17.9 Hz, 1H), 4.62 (q, J=7.1 Hz, 2H); $^{13}$C NMR (100 MHz, $CDCl_3$) δ ppm −4.9 ($CH_3$), −4.4 ($CH_3$), 13.9 ($CH_3$), 18.1 (C), 21.0 ($CH_3$), 25.9 (2×$CH_3$), 42.8 ($CH_2$), 70.6 ($CH_2$), 75.0 (CH), 205.7 (C), 213.6 (C); Mass (ESI+) m/z (%) 345 (100) [M+Na]$^+$, 323 (8).

3. A Method for Preparing Cyclic Peptides of Formula (IV)

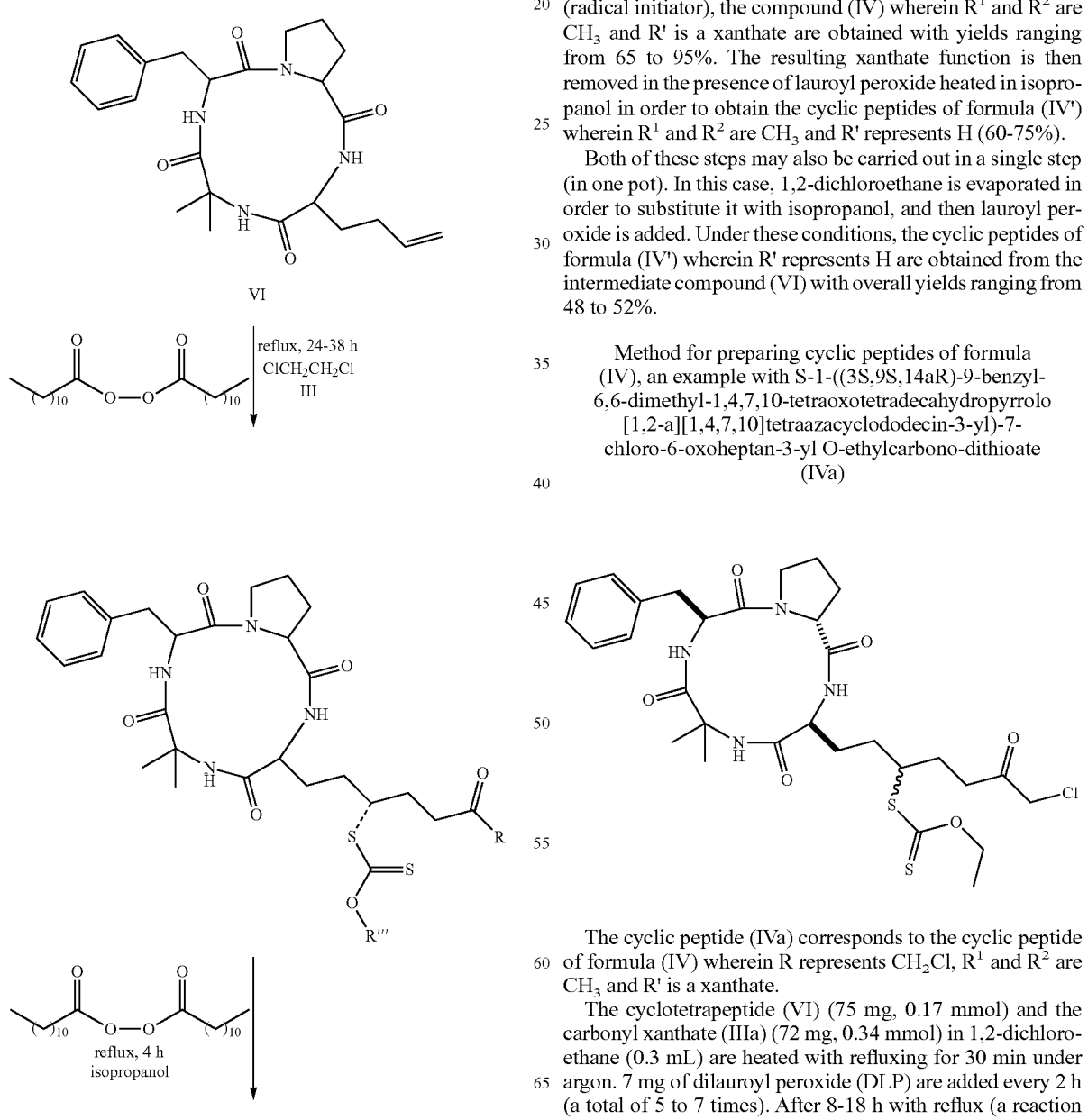

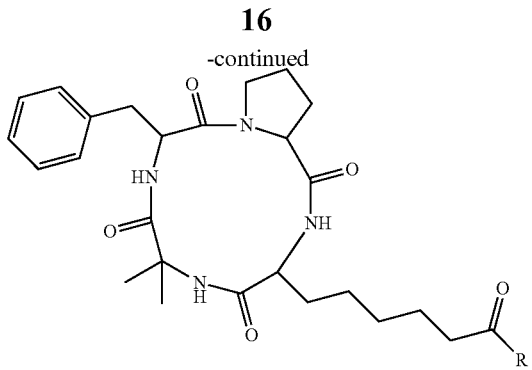

From the intermediate compound of formula (VI), radical conditions were applied with different carbonyl xanthates (III) for installing the carbonyl group in position 8 (see the scheme 3 above). After heating in 1,2-dichloroethane in the presence of carbonyl xanthate (III) and of lauroyl peroxide (radical initiator), the compound (IV) wherein R$^1$ and R$^2$ are $CH_3$ and R' is a xanthate are obtained with yields ranging from 65 to 95%. The resulting xanthate function is then removed in the presence of lauroyl peroxide heated in isopropanol in order to obtain the cyclic peptides of formula (IV') wherein R$^1$ and R$^2$ are $CH_3$ and R' represents H (60-75%).

Both of these steps may also be carried out in a single step (in one pot). In this case, 1,2-dichloroethane is evaporated in order to substitute it with isopropanol, and then lauroyl peroxide is added. Under these conditions, the cyclic peptides of formula (IV') wherein R' represents H are obtained from the intermediate compound (VI) with overall yields ranging from 48 to 52%.

Method for preparing cyclic peptides of formula (IV), an example with S-1-((3S,9S,14aR)-9-benzyl-6,6-dimethyl-1,4,7,10-tetraoxotetradecahydropyrrolo[1,2-a][1,4,7,10]tetraazacyclododecin-3-yl)-7-chloro-6-oxoheptan-3-yl O-ethylcarbono-dithioate (IVa)

The cyclic peptide (IVa) corresponds to the cyclic peptide of formula (IV) wherein R represents $CH_2Cl$, R$^1$ and R$^2$ are $CH_3$ and R' is a xanthate.

The cyclotetrapeptide (VI) (75 mg, 0.17 mmol) and the carbonyl xanthate (IIIa) (72 mg, 0.34 mmol) in 1,2-dichloroethane (0.3 mL) are heated with refluxing for 30 min under argon. 7 mg of dilauroyl peroxide (DLP) are added every 2 h (a total of 5 to 7 times). After 8-18 h with reflux (a reaction followed by TLC), the solvent is evaporated and the product is directly purified by flash chromatography on silica gel (for (IVa), 40% EtOAc/cyclohexane) in order to obtain (IVa) (72 mg, 65%) in the form of a colorless lacquer. $R_f$=0.16 (40% EtOAc/cyclohexane); IR $v_{max}$ (film) 3302, 2925, 1734, 1678, 1663, 1628, 1525, 1435, 1390, 1217, 1111, 1048 cm$^{-1}$; $^1$H NMR (400 MHz, CDCl$_3$) δ ppm 1.35 (s, 3H), 1.43 (t, J=7.1 Hz, 3H), 1.62-1.96 (m, 10H), 2.07-2.23 (m, 2H), 2.32 (m, 1H), 2.76 (m, 2H), 2.95 (dd, J=13.5, 5.7 Hz, 1H), 3.23 (m, 1H), 3.26 (dd, J=13.5, 10.2 Hz, 1H), 3.76 (m, 1H), 3.86 (m, 1H), 4.08 (s, 2H), 4.22 (m, 1H), 4.65 (q, J=7.1 Hz, 2H), 4.66 (m, 1H), 5.17 (m, 1H), 5.92 (s, NH), 7.15 (bd, J=10.1 Hz, NH), 7.19-7.32 (m, 5H), 7.47 (bd, J=10.1 Hz, NH); $^{13}$C NMR (100 MHz, CDCl$_3$) δ ppm 14.0 (CH$_3$), 23.7 (CH$_3$), 24.9 (CH$_2$), 25.2 (CH$_2$), 26.7 (CH$_3$), 28.0 (CH$_2$), 29.9 (CH$_2$), 31.1 (CH$_2$), 36.0 (CH$_2$), 37.0 (CH$_2$), 47.2 (CH$_2$), 48.4 (CH$_2$), 50.7 (CH), 53.6 (CH), 54.3 (CH), 58.0 (CH), 59.0 (C), 70.5 (CH$_2$), 126.9 (CH), 128.8 (2×CH), 129.2 (2×CH), 137.2 (C), 172.1 (C), 173.1 (C), 174.1 (C), 175.7 (C), 202.0 (C), 214.3 (C); Mass (ESI+) m/z (%) 675 (100) [M+Na]$^+$, 653 (32); HRMS (ESI+): m/z calculated for C$_{30}$H$_{41}$N$_4$O$_6$ClNaS$_2$ 675.2054. found 675.2053.

Preparation of benzyl 6-((3S,9S,14aR)-9-benzyl-6,6-dimethyl-1,4,7,10-tetraoxotetra-decahydropyrrolo[1,2-a][1,4,7,10]tetraazacyclododecin-3-yl)-4-(ethoxy-carbono-thioyl-thio)hexanoate (IVc)

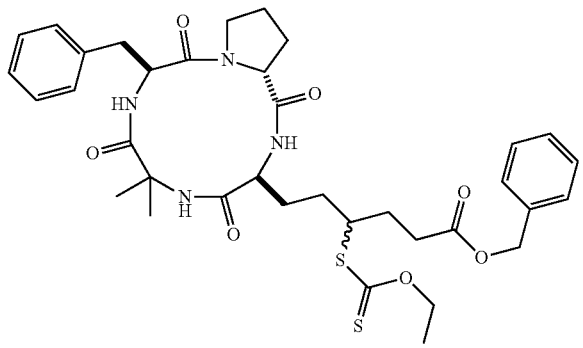

According to the procedure described above, a product (IVc), purified by flash chromatography (1% MeOH/CH$_2$Cl$_2$), % yield=90%; $R_f$=0.06 (1% MeOH/CH$_2$Cl$_2$); IR $v_{max}$ (film) 3308, 2940, 1734, 1681, 1663, 1629, 1525, 1454, 1436, 1215, 1111, 1049, 910 cm$^{-1}$; $^1$H NMR (400 MHz, CDCl$_3$) δ ppm 1.34 (s, 3H), 1.41 (t, J=7.1 Hz, 3H), 1.65-1.81 (m, 8H), 1.86-2.00 (m, 2H), 2.05-2.26 (m, 2H), 2.32 (m, 1H), 2.52 (m, 2H), 2.95 (dd, J=13.5, 5.7 Hz, 1H), 3.23 (m, 1H), 3.26 (dd, J=13.5, 10.1 Hz, 1H), 3.79 (m, 1H), 3.86 (m, 1H), 4.21 (m, 1H), 4.62 (q, J=7.1 Hz, 2H), 4.66 (m, 1H), 5.12 (s, 2H), 5.17 (m, 1H), 5.92 (s, NH), 7.13 (bd, J=10.2 Hz, NH), 7.19-7.39 (m, 10H), 7.47 (bd, J=10.2 Hz, NH); $^{13}$C NMR (100 MHz, CDCl$_3$) δ ppm 13.8 (CH$_3$), 23.5 (CH$_3$), 24.7 (CH$_2$), 25.0 (CH$_2$), 26.2 (CH$_2$), 26.5 (CH$_3$), 29.2 (CH$_2$), 30.6 (CH$_2$), 31.5 (CH$_2$), 35.8 (CH$_2$), 47.0 (CH$_2$), 50.4 (CH), 53.4 (CH), 54.1 (CH), 57.8 (CH), 58.8 (C), 66.4 (CH$_2$), 70.1 (CH$_2$), 126.7 (CH), 128.3 (2×CH), 128.6 (2×CH), 128.7 (2×CH), 129.0 (2×CH), 135.8 (C), 137.0 (C), 171.9 (C), 172.7 (C), 172.8 (C), 173.9 (C), 175.6 (C), 213.9 (C); Mass (ESI+) m/z (%) 733 (100) [M+Na]$^+$, 711 (46), 463 (25); HRMS (ESI+): m/z calculated for C$_{36}$H$_{46}$N$_4$O$_7$NaS$_2$ 733.2706. found 733.2709.

Preparation of S—(R)-1-((3S,9S,14aR)-9-benzyl-6,6-dimethyl-1,4,7,10-tetraoxotetra-decahydropyrrolo [1,2-a][1,4,7,10]tetraazacyclododecin-3-yl)-7-(tert-butyldimethylsilyl-oxy)-6-oxooctan-3-yl O-ethyl carbonodithioate (IVf)

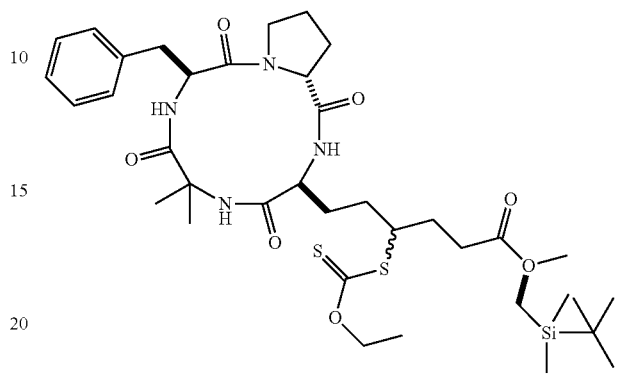

According to the procedure described above, a product (IVf), purified by flash chromatography (0.8% MeOH/CH$_2$Cl$_2$), % yield=96%; $R_f$=0.1 (1% MeOH/CH$_2$Cl$_2$); $^1$H NMR (400 MHz, CDCl$_3$) δ ppm 0.07 (s, 6H), 0.91 (s, 9H), 1.28 (m, 3H), 1.34 (s, 3H), 1.42 (t, J=7.1 Hz, 3H), 1.62-1.88 (m, 9H), 1.92-2.11 (m, 2H), 2.18 (m, 1H), 2.33 (m, 1H), 2.76 (m, 2H), 2.96 (dd, J=13.5, 5.7 Hz, 1H), 3.23 (m, 1H), 3.27 (dd, J=13.5, 10.1 Hz, 1H), 3.77 (m, 1H), 3.86 (m, 1H), 4.14 (q, J=6.7 Hz, 1H), 4.22 (m, 1H), 4.63 (q, J=7.1 Hz, 2H), 4.66 (m, 1H), 5.17 (m, 1H), 5.96 (s, NH), 7.15 (d, J=10.1 Hz, NH), 7.18-7.30 (m, 5H), 7.51 (bd, J=10.1 Hz, NH); $^{13}$C NMR (100 MHz, CDCl$_3$) δ ppm −4.8 (CH$_3$), −4.5 (CH$_3$), 14.0 (CH$_3$), 18.2 (CH$_3$), 23.7 (CH$_3$), 24.9 (CH$_2$), 25.2 (CH$_2$), 25.9 (3×CH$_3$), 26.4 (CH$_2$), 26.7 (CH$_2$), 27.6 (CH$_2$), 31.4 (CH$_2$), 34.5 (CH$_2$), 36.0 (CH$_2$), 47.2 (CH$_2$), 51.1 (CH), 53.6 (CH), 54.3 (CH), 58.0 (CH), 59.0 (C), 70.2 (CH$_2$), 75.0 (CH), 126.9 (CH), 128.8 (2×CH), 129.2 (2×CH), 137.2 (C), 172.1 (C), 173.0 (C), 174.1 (C), 175.8 (C), 213.5 (C), 214.4 (C); Mass (ESI+) m/z (%) 785 (90) [M+Na]$^+$, 763 (70), 413 (100); HRMS (ESI+): m/z calculated for C$_{37}$H$_{58}$N$_4$O$_7$NaSiS$_2$ 785.3414. found 785.3407.

Preparation of S—(S)-1-((3S,9S,14aR)-9-benzyl-6,6-dimethyl-1,4,7,10-tetraoxotetra-decahydropyrrolo [1,2-a][1,4,7,10]tetraazacyclododecin-3-yl)-7-(tert-butyldimethyl-silyloxy)-6-oxooctan-3-yl O-ethyl carbonodithioate (IVg)

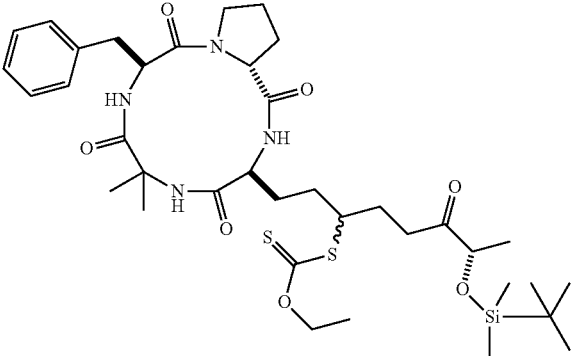

According to the procedure described above, a product (IVg), purified by flash chromatography (0.8% MeOH/CH$_2$Cl$_2$), % yield=95%; R$_f$=0.1 (1% MeOH/CH$_2$Cl$_2$); $^1$H NMR (400 MHz, CDCl$_3$) δ ppm 0.07 (s, 6H), 0.91 (s, 9H), 1.26 (m, 3H), 1.35 (s, 3H), 1.42 (t, J=7.1 Hz, 3H), 1.60-1.86 (m, 9H), 1.90-2.08 (m, 2H), 2.17 (m, 1H), 2.33 (m, 1H), 2.76 (m, 2H), 2.95 (dd, J=13.5, 5.7 Hz, 1H), 3.23 (m, 1H), 3.26 (dd, J=13.5, 10.1 Hz, 1H), 3.77 (m, 1H), 3.86 (m, 1H), 4.13 (q, J=6.7 Hz, 1H), 4.24 (m, 1H), 4.63 (q, J=7.1 Hz, 2H), 4.67 (m, 1H), 5.17 (m, 1H), 6.00 (bs, NH), 7.15 (d, J=10.1 Hz, NH), 7.18-7.30 (m, 5H), 7.50 (bd, J=10.1 Hz, NH); $^{13}$C NMR (100 MHz, CDCl$_3$) δ ppm −4.9 (CH$_3$), −4.5 (CH$_3$), 14.0 (CH$_3$), 18.2 (CH$_3$), 23.7 (CH$_3$), 24.9 (CH$_2$), 25.2 (CH$_2$), 25.9 (3×CH$_3$), 26.4 (CH$_2$), 26.6 (CH$_3$), 27.6 (CH$_2$), 31.2 (CH$_2$), 34.4 (CH$_2$), 36.0 (CH$_2$), 47.1 (CH$_2$), 51.0 (CH), 53.6 (CH), 54.5 (CH), 58.0 (CH), 59.0 (C), 70.2 (CH$_2$), 75.0 (CH), 126.9 (CH), 128.8 (2×CH), 129.2 (2×CH), 137.2 (C), 172.0 (C), 173.0 (C), 174.1 (C), 175.8 (C), 213.6 (C), 214.3 (C); Mass (ESI+) m/z (%) 785 (100) [M+Na]$^+$, 763 (30); HRMS (ESI+): m/z calculated for C$_{37}$H$_{58}$N$_4$O$_7$NaSiS$_2$ 785.3414. found 785.3431.

General procedure for obtaining (IV') from (IV) (a two-step approach), an example with (3S,9S,14aR)-9-benzyl-3-(7-chloro-6-oxoheptyl)-6,6-dimethyl-decahydropyrrolo[1,2-a][1,4,7,10]tetraazacyclododecine-1,4,7,10-tetraone (IV'a)

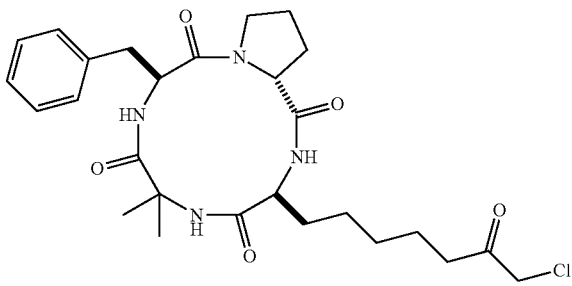

The cyclic peptide (IV'a) corresponds to the cyclic peptide of formula (IV) wherein R represents CH$_2$Cl, R$^1$ and R$^2$ are CH$_3$ and R' represents H. Further, two bonds have a defined configuration.

The cyclic peptide (IVa) (12 mg, 0.018 mmol) in isopropanol (1 mL) is heated with reflux for 5 h in the presence of DLP (11 mg, 0.027 mmol). After evaporation and flash chromatography (silica gel, 30% EtOAc/cyclohexane), the product (IV'a) (9 mg, 92%) is obtained as a colorless lacquer. R$_f$=0.07 (40% EtOAc/cyclohexane); [α]$^D$=−80 (c=1.0, CHCl$_3$); IR ν$_{max}$ (film) 3304, 2928, 1733, 1678, 1663, 1628, 1525, 1434, 1390, 1179 cm$^{-1}$; $^1$H NMR (400 MHz, CDCl$_3$) δ ppm 1.29-1.34 (m, 7H), 1.63 (m, 2H), 1.69-1.87 (m, 7H), 2.17 (m, 1H), 2.32 (m, 1H), 2.56 (t, J=7.3 Hz, 2H), 2.95 (dd, J=13.5, 5.7 Hz, 1H), 3.21 (dd, J=10.0, 7.0 Hz, 1H), 3.26 (dd, J=13.5, 10.0 Hz, 1H), 3.86 (m, 1H), 4.07 (s, 2H), 4.19 (ddd, J=10.2, 7.6, 7.6 Hz, 1H), 4.67 (m, 1H), 5.16 (ddd, J=10.1, 10.0, 5.7 Hz, 1H), 5.95 (s, NH), 7.11 (bd, J=10.1 Hz, NH), 7.19-7.29 (m, 5H), 7.51 (bd, J=10.1 Hz, NH); $^{13}$C NMR (100 MHz, CDCl$_3$) δ ppm 23.4 (CH$_2$), 23.7 (CH$_3$), 24.9 (CH$_2$), 25.2 (CH$_2$), 25.4 (CH$_2$), 26.7 (CH$_3$), 28.8 (CH$_2$), 28.9 (CH$_2$), 36.0 (CH$_2$), 39.6 (CH$_2$), 47.1 (CH$_2$), 48.3 (CH$_2$), 53.6 (CH), 54.4 (CH), 57.9 (CH), 59.0 (C), 126.9 (CH), 128.8 (2×CH), 129.2 (2×CH), 137.2 (C), 172.0 (C), 173.0 (C), 175.0 (C), 175.8 (C), 202.7 (C); Mass (ESI+) m/z (%) 555 (100) [M+Na]$^+$, 533 (10); HRMS (ESI+): m/z calculated for C$_{27}$H$_{37}$N$_4$O$_5$ClNaS$_2$ 555.2350. found 555.2343.

Preparation of benzyl 6-((3S,9S,14aR)-9-benzyl-6,6-dimethyl-1,4,7,10-tetraoxotetra-decahydropyrrolo[1,2-a][1,4,7,10]tetraazacyclododecin-3-yl)hexanoate (IV'c)

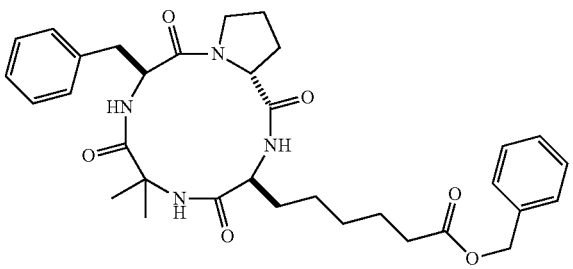

From (IVc), the product (IV'c) is obtained after purification by flash chromatography (1% MeOH/CH$_2$Cl$_2$), % yield=69%; R$_f$=0.17 (40% EtOAc/cyclohexane); [α]$^D$=−75 (c=1.4, CHCl$_3$); IR ν$_{max}$ (film) 3309, 2934, 1735, 1678, 1663, 1629, 1525, 1424, 1257, 1173 cm$^{-1}$; $^1$H NMR (400 MHz, CDCl$_3$) δ ppm 1.25-1.40 (m, 7H), 1.65 (m, 2H), 1.72 (m, 1H), 1.77-187 (m, 6H), 2.17 (m, 1H), 2.29 (m, 1H), 2.35 (t, J=7.5 Hz, 2H), 2.95 (dd, J=13.5, 5.7 Hz, 1H), 3.19-3.29 (m, 2H), 3.86 (ddd, J=10.3, 8.6, 4.6 Hz, 1H), 4.18 (ddd, J=10.2, 7.6, 7.6 Hz, 1H), 4.65 (m, 1H), 5.11 (s, 2H), 5.16 (ddd, J=10.2, 10.1, 5.7, 1H), 5.90 (s, NH), 7.09 (bd, J=10.2 Hz, NH), 7.17-7.40 (m, 10H), 7.51 (bd, J=10.3 Hz, NH); $^{13}$C NMR (100 MHz, CDCl$_3$) δ ppm 23.7 (CH$_3$), 24.86 (CH$_2$), 24.93 (CH$_2$), 25.2 (CH$_2$), 25.4 (CH$_2$), 26.7 (CH$_3$), 28.9 (2×CH$_2$), 34.3 (CH$_2$), 36.0 (CH$_2$), 47.2 (CH$_2$), 53.6 (CH), 54.5 (CH), 58.0 (CH), 59.0 (C), 66.3 (CH$_2$), 126.9 (CH), 128.4 (2×CH), 128.7 (2×CH), 128.8 (2×CH), 129.2 (2×CH), 136.2 (C), 137.2 (C), 172.0 (C), 173.0 (C), 173.6 (C), 174.5 (C), 175.8 (C); Mass (ESI+) m/z (%) 613 (100) [M+Na]$^+$, 591 (18); HRMS (ESI+): m/z calculated for C$_{33}$H$_{42}$N$_4$O$_6$Na, 613.3002. found 613.2991.

Preparation of (3S,9S,14aR)-9-benzyl-3-((S)-7-(tert-butyldimethylsilyloxy)-6-oxooctyl)-6,6-dimethyl-decahydropyrrolo[1,2-a][1,4,7,10]tetraazacyclododecine-1,4,7,10-tetraone (IV'g)

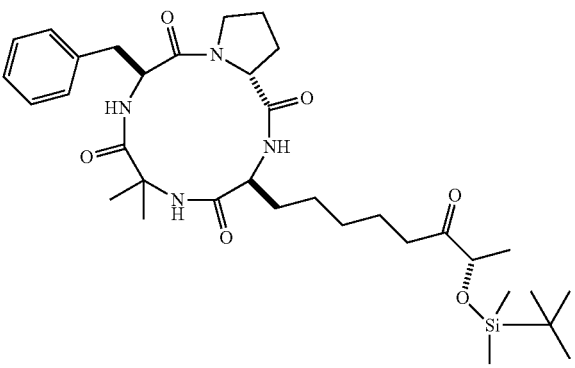

From (IVg), the product (IV'g) is obtained after purification by flash chromatography (0.8% MeOH/CH$_2$Cl$_2$), % yield=59%; $^1$H NMR (400 MHz, CDCl3) δ ppm 0.07 (s, 6H), 0.91 (s, 9H), 1.25-1.34 (m, 9H), 1.55 (m, 2H), 1.63 (m, 2H), 1.76 (m, 1H), 1.77 (s, 3H), 2.17 (m, 1H), 2.32 (m, 1H), 2.47-2.64 (m, 2H), 2.95 (dd, J=13.5, 5.7 Hz, 1H), 3.21 (m, 1H), 3.26 (dd, J=13.5, 10.1 Hz, 1H), 3.86 (m, 1H), 4.13 (q, J=6.8 Hz, 1H), 4.20 (ddd, J=10.1, 7.6, 7.6 Hz, 1H), 4.67 (bd, J=7.6 Hz, H1), 5.17 (m, 1H), 6.11 (bs, NH), 7.15 (d, J=10.1 Hz, NH), 7.18-7.29 (m, 5H), 7.57 (bd, J=10.1 Hz, NH); $^{13}$C NMR (100 MHz, CDCl3) δ ppm −4.9 (CH3), −4.5 (CH3), 21.0 (CH3), 22.9 (CH2), 23.1 (CH2), 23.8 (CH3), 24.9 (CH2), 25.2 (CH2), 25.9 (3×CH3), 26.6 (CH3), 29.8 (CH2), 29.9 (CH2), 36.0 (CH2), 36.9 (CH2), 47.1 (CH2), 53.6 (CH), 54.6 (CH), 58.0 (CH), 58.9 (C), 75.1 (CH), 126.9 (CH), 128.8 (2×CH), 129.2 (2×CH), 137.2 (C), 172.0 (C), 173.0 (C), 174.5 (C), 175.8 (C), 214.3 (C); Mass (ESI+) m/z (%) 665 (100) [M+Na]+, 643 (30).

Preparation of (3S,9S,14aR)-9-benzyl-3-((R)-7-(tert-butyldimethylsilyloxy)-6-oxooctyl)-6,6-dimethyl-decahydropyrrolo[1,2-a][1,4,7,10]tetraazacyclododecine-1,4,7,10-tetraone (IV′f)

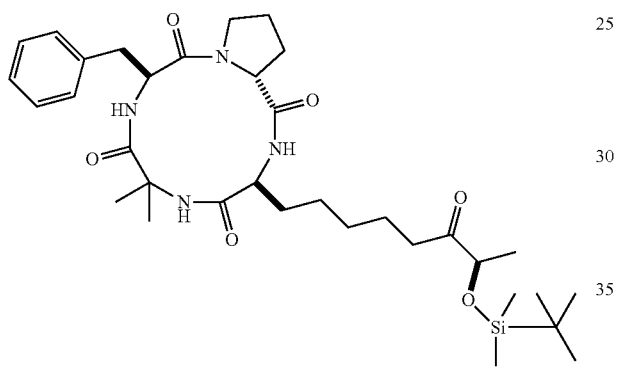

From (IVf), the product (IV′f) is obtained after purification by flash chromatography (0.8% MeOH/CH2Cl2), % yield=60%; [α]$^D$=−47 (c=2.3, CHCl3); $^1$H NMR (400 MHz, CDCl3) δ ppm 0.07 (s, 6H), 0.91 (s, 9H), 1.26-1.34 (m, 7H), 1.34 (s, 3H), 1.55-1.73 (m, 4H), 1.75 (m, 1H), 1.77 (s, 3H), 2.17 (m, 1H), 2.32 (m, 1H), 2.47-2.64 (m, 2H), 2.95 (dd, J=13.5, 5.7 Hz, 1H), 3.21 (m, 1H), 3.26 (dd, J=13.5, 10.1 Hz, 1H), 3.86 (m, 1H), 4.13 (q, J=6.8 Hz, 1H), 4.19 (ddd, J=10.1, 7.6, 7.6 Hz, 1H), 4.66 (bd, J=7.8 Hz, 1H), 5.16 (m, 1H), 6.03 (s, NH), 7.12 (d, J=10.1 Hz, NH), 7.18-7.29 (m, 5H), 7.55 (bd, J=10.1 Hz, NH); $^{13}$C NMR (100 MHz, CDCl3) δ ppm −4.8 (CH3), −4.5 (CH3), 21.1 (CH3), 22.9 (CH2), 23.2 (CH2), 23.8 (CH3), 25.0 (CH2), 25.2 (CH2), 26.0 (3×CH3), 26.7 (CH2), 29.8 (CH2), 29.9 (CH2), 36.0 (CH2), 36.9 (CH2), 47.2 (CH2), 53.7 (CH), 54.6 (CH), 58.0 (CH), 59.0 (C), 75.1 (CH), 126.9 (CH), 128.8 (2×CH), 129.3 (2×CH), 137.3 (C), 172.0 (C), 173.0 (C), 174.6 (C), 175.9 (C), 214.4 (C); Mass (ESI+) m/z (%) 665 (17) [M+Na]+, 551 (100); HRMS (ESI+): m/z calculated for $C_{34}H_{54}N_4O_6NaS_i$ 665.3710. found 665.3717.

According to another embodiment (scheme 4), the terminal alkene of the intermediate compound (VI) is substituted differently by carrying out another type of radical reaction. For example, the reaction with thio-acetic acid (XVII) (for example $R^a$=an alkyl group containing between 1 and 10 carbon atoms as a linear or branched chain, notably CH3) on the intermediate (VI) in the presence of a radical initiator (AIBN) leads to the formation of the cyclic tetrapeptide thio-ester (XVIII) (91%).

Scheme 4

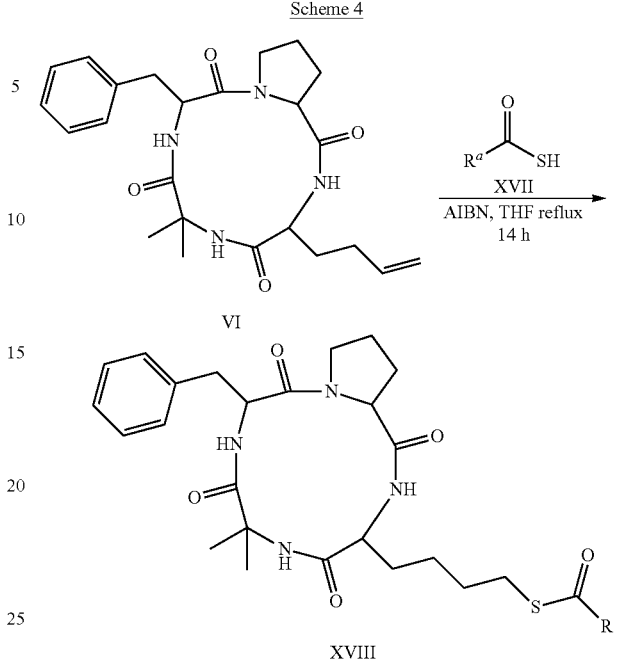

Preparation of S-4-((3S,9S,14aR)-9-benzyl-6,6-dimethyl-1,4,7,10-tetraoxotetradeca-hydropyrrolo[1,2-a][1,4,7,10]tetraazacyclododecin-3-yl)butyl ethanethioate (XVIIIa)

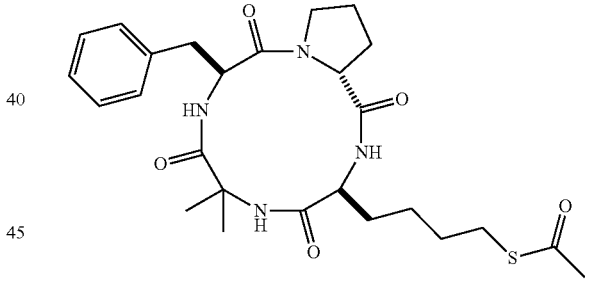

The compound (VI) (32 mg, 0.073 mmol) in anhydrous THF (10 mL) is added with thioacetic acid (22 mg, 0.29 mmol). The solution is heated with reflux for 30 min under argon. A catalytic amount of AIBN is added and the reaction is stirred with reflux for 16 h. After evaporation of the solvent, the residue is directly purified by flash chromatography (1% MeOH/CH2Cl2) in order to obtain the product (XVIIIa) (34 mg, 91%).

$R_f$=0.12 (1% MeOH/CH2Cl2); IR $v_{max}$ (film) 3307, 2934, 1684, 1630, 1528, 1428, 1274, 1187, 915 cm$^{−1}$; $^1$H NMR (400 MHz, CDCl3) δ ppm 1.34 (s, 3H), 1.39 (m, 2H), 1.53-1.71 (m, 4H), 1.72 (m, 5H), 2.11-2.22 (m, 2H), 2.32 (s, 3H), 2.85 (t, J=7.2 Hz, 2H), 2.95 (dd, J=13.4, 5.6 Hz, 1H), 3.23 (m, 1H), 3.26 (m, 1H), 3.86 (m, 1H), 4.21 (m, 1H), 4.68 (m, 1H), 5.17 (s, 1H), 6.02 (s, NH), 7.13 (d, J=10.1 Hz, NH), 7.19-7.29 (m, 5H), 7.53 (d, J=10.1 Hz, NH); $^{13}$C NMR (100 MHz, CDCl3) δ ppm 23.7 (CH3), 24.8 (CH2), 24.9 (CH2), 25.1 (CH2), 26.6 (CH2), 28.6 (CH2), 28.9 (CH2), 29.33 (CH2), 30.8 (CH3), 35.9 (CH2), 47.1 (CH2), 53.6 (CH), 54.4 (CH), 57.9 (CH), 58.9 (C), 126.9 (CH), 128.8 (2×CH), 129.2 (2×CH), 137.2 (C), 172.0 (C), 173.0 (C), 174.4 (C), 175.8 (C), 196.0 (C); Mass (ESI+) m/z (%) 539 (100) [M+Na]$^+$, 517 (10); HRMS (ESI+): m/z calculated for C$_{26}$H$_{36}$N$_4$O$_5$NaS 539.2304. found 539.2302.

General Procedure for Obtaining (IV') from (VI) in One Pot, an Example of (IV'f)

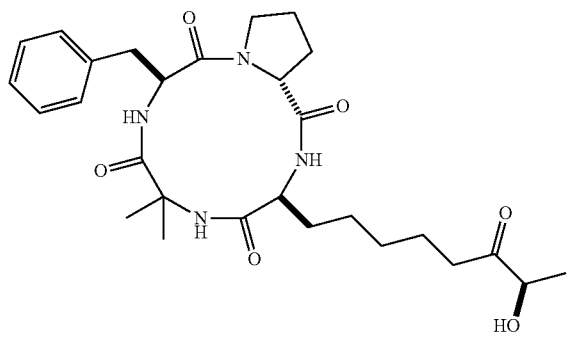

The cyclotetrapeptide (VI) (31 mg, 0.07 mmol) and carbonyl xanthate (IIIf) (45 mg, 0.14 mmol) in 1,2-dichloroethane (0.2 mL) are heated with reflux for 30 min under argon. 3 mg of dilauroyl peroxide (DLP) are added every 2 h (a total of 5 to 7 times). After 18 h with reflux (reaction tracked by TLC), the solvent is evaporated and replaced with isopropanol (1.5 mL). The solution is refluxed for 30 min under argon, and then some DLP (28 mg, 0.07 mmol) is added. The solution is heated with reflux for 1 h, and then some DLP is again added (14 mg, 0.035 mmol). The mixture is heated for a further 3 h. After evaporation, the product is directly purified by chromatography (silica gel, 25% EtOAc/cyclohexane) in order to obtain the product (IV'f) (22 mg, 48%).

Preparation of (3S,9S,14aR)-9-benzyl-6,6-dimethyl-3-(7,7,7-trifluoro-6-oxoheptyl)-decahydropyrrolo[1,2-a][1,4,7,10]tetraazacyclododecine-1,4,7,10-tetraone (IV'b)

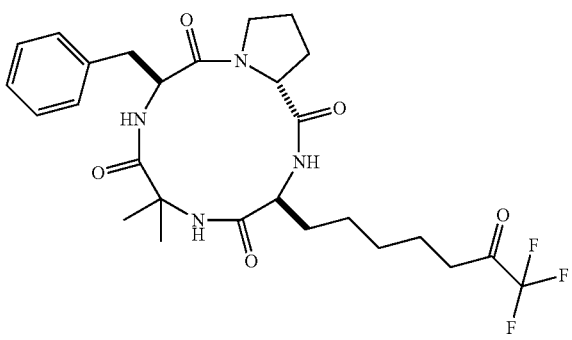

The product (IV'b) is obtained after purification by flash chromatography (35% EtOAc/cyclohexane), % yield=49%; R$_f$=0.08 (40% EtOAc/cyclohexane); [α]$^D$=−71 (c=0.44, CHCl$_3$); $^1$H NMR (400 MHz, CDCl$_3$) δ ppm 1.25-1.36 (m, 7H), 1.56-1.72 (m, 4H), 1.77 (m, 1H), 1.77 (s, 3H), 2.18 (m, 1H), 2.33 (m, 1H), 2.71 (t, J=7.2 Hz, 2H), 2.95 (dd, J=13.5, 5.7 Hz, 1H), 3.22 (m, 1H), 3.26 (dd, J=13.5, 10.1 Hz, 1H), 3.87 (m, 1H), 4.19 (m, 1H), 4.66 (bd, J=7.8 Hz, 1H), 5.17 (ddd, J=10.1, 10.1, 5.7 Hz, 1H), 5.92 (s, NH), 7.12 (d, J=10.2 Hz, NH), 7.19-7.31 (m, 5H), 7.49 (d, J=10.2 Hz, NH); IR ν$_{max}$ (thin film, CH$_2$Cl$_2$) 3307, 2925, 1763, 1683, 1666, 1631, 1529, 1435, 1206, 1174 cm$^{-1}$; Mass (ESI+) m/z (%) 575 (100) [M+Na]$^+$, 437 (12); HRMS (ESI+): m/z calculated for C$_{27}$H$_{35}$N$_4$O$_5$F$_3$Na, 575.2457. found 575.2442.

Preparation of (3S,9S,14aR)-9-benzyl-6,6-dimethyl-3-(6-oxooctyl)decahydro-pyrrolo[1,2-a][1,4,7,10]tetraazacyclododecine-1,4,7,10-tetraone (IV'd)

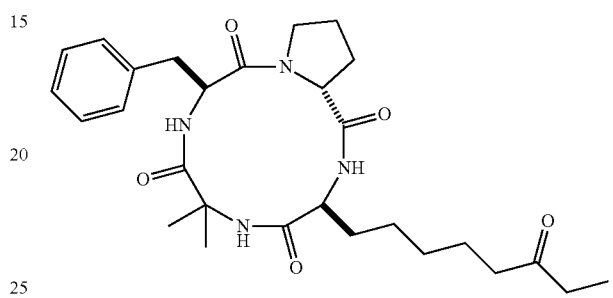

The product (IV'd) is obtained after purification by flash chromatography (30% EtOAc/cyclohexane), % yield=50%; R$_f$=0.1 (40% EtOAc/cyclohexane); [α]$^D$=−65 (c=0.47, CHCl$_3$); IR ν$_{max}$ (film) 2923, 1716, 1683, 1540, 1522, 1457, 1177 cm$^{-1}$; $^1$H NMR (400 MHz, CDCl$_3$) δ ppm 1.05 (t, J=7.3 Hz, 3H), 1.25-1.34 (m, 4H), 1.34 (s, 3H), 1.51-1.70 (m, 4H), 1.77 (m, 1H), 1.77 (s, 3H), 2.18 (m, 1H), 2.32 (m, 1H), 2.39 (t, J=7.3 Hz, 2H), 2.41 (q, J=7.3 Hz, 2H), 2.95 (dd, J=13.5, 5.7 Hz, 1H), 3.22 (m, 1H), 3.26 (dd, J=13.5, 9.9 Hz, 1H), 3.86 (m, 1H), 4.18 (m, 1H), 4.66 (bd, J=8.0 Hz, 1H), 5.16 (ddd, J=10.1, 10.1, 5.8 Hz, 1H), 5.89 (s, NH), 7.08 (d, J=10.2 Hz, NH), 7.18-7.31 (m, 5H), 7.51 (d, J=10.2 Hz, NH); $^{13}$C NMR (100 MHz, CDCl$_3$) δ ppm 8.1 (CH$_3$), 23.8 (CH$_3$), 25.0 (CH$_2$), 25.2 (CH$_2$), 25.6 (CH$_2$), 26.7 (CH$_3$), 29.0 (CH$_2$), 29.9 (CH$_2$), 36.0 (CH$_2$), 36.1 (CH$_2$), 42.4 (CH$_2$), 47.2 (CH$_2$), 53.6 (CH), 54.5 (CH), 58.0 (CH), 59.0 (C), 126.9 (CH), 128.8 (2×CH), 129.2 (2×CH), 137.2 (C), 172.0 (C), 173.0 (C), 174.6 (C), 175.9 (C), 211.8 (C); Mass (ESI+) m/z (%) 535 (100) [M+Na]$^+$, 437 (33).

Preparation of ethyl 8-((3S,9S,14aR)-9-benzyl-6,6-dimethyl-1,4,7,10-tetraoxotetra-decahydropyrrolo[1,2-a][1,4,7,10]tetraazacyclododecin-3-yl)-3-oxooctanoate (IV'e)

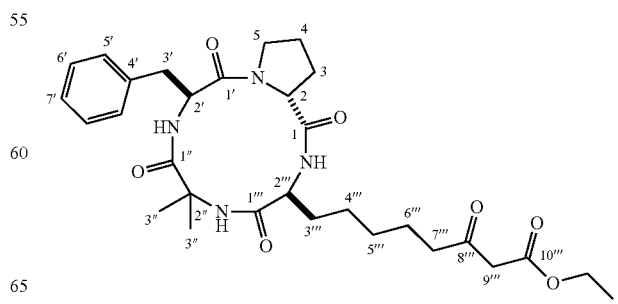

The product (IV'e) is obtained after purification by flash chromatography (35% EtOAc/cyclohexane), % yield=52%; $R_f$=0.05 (40% EtOAc/cyclohexane); $[\alpha]^D$=−71 (c=0.68, CHCl$_3$); IR $v_{max}$ (film) 3305, 2928, 1741, 1714, 1681, 1666, 1629, 1529, 1434, 1315, 1232, 1178, 1030 cm$^{-1}$; $^1$H NMR (400 MHz, CDCl$_3$) δ ppm 1.28 (t, J=7.1 Hz, 3H), 1.25-1.34 (m, 4H), 1.34 (s, 3H), 1.54-1.67 (m, 4H), 1.77 (m, 1H), 1.77 (s, 3H), 2.17 (m, 1H), 2.32 (m, 1H), 2.53 (t, J=7.3 Hz, 2H), 2.95 (dd, J=13.5, 5.7 Hz, 1H), 3.23 (m, 1H), 3.26 (dd, J=13.4, 10.0 Hz, 1H), 3.42 (s, 2H), 3.86 (m, 1H), 4.17 (m, 1H), 4.20 (q, J=7.1 Hz, 2H), 4.66 (bd, J=7.8 Hz, 1H), 5.16 (ddd, J=10.1, 10.1, 5.8 Hz, 1H), 5.92 (s, NH), 7.09 (d, J=10.2 Hz, NH), 7.19-7.32 (m, 5H), 7.51 (d, J=10.1 Hz, NH); $^{13}$C NMR (100 MHz, CDCl$_3$) δ ppm 14.3 (CH$_3$), 23.3 (CH$_2$), 23.8 (CH$_3$), 25.0 (CH$_2$), 25.2 (CH$_2$), 25.5 (CH$_2$), 26.7 (CH$_3$), 28.8 (CH$_2$), 28.9 (CH$_2$), 36.0 (CH$_2$), 43.0 (CH$_2$), 47.2 (CH$_2$), 49.5 (CH$_2$), 53.6 (CH), 54.5 (CH), 58.0 (CH), 59.0 (C), 61.6 (CH$_2$), 126.9 (CH), 128.8 (2×CH), 129.2 (2×CH), 137.2 (C), 167.4 (C), 172.0 (C), 173.0 (C), 174.5 (C), 175.8 (C), 202.9 (C); Mass (ESI+) m/z (%) 593 (100) [M+Na]$^+$, 521 (20); HRMS (ESI+): m/z calculated for C$_{30}$H$_{42}$N$_4$O$_7$Na, 593.2951. found 593.2942.

4. Method for Preparing Cyclic Peptides of Formula (IV'f) and (IV'g)

Scheme 5

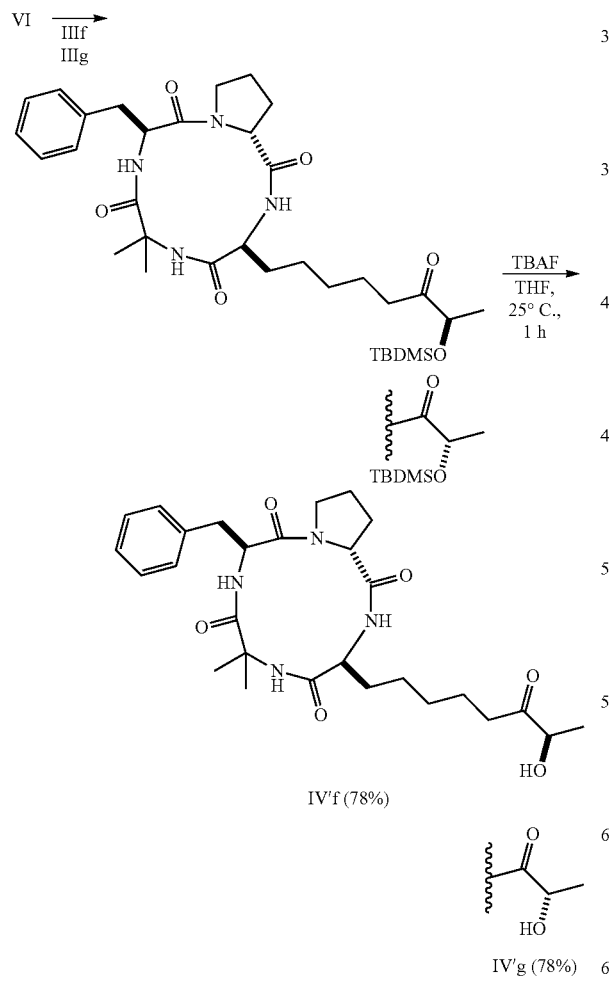

IV'f (78%)

According to an embodiment of the invention, the intermediate compound of formula (VII) is reacted with carbonyl xanthate of formula (IIIf) (see scheme 2) and in a second step, it is proceeded with de-protection of the obtained compound. The compound (IV'f) is thereby obtained. According to another embodiment of the invention, the intermediate compound of formula (VII) is reacted with carbonyl xanthate of formula (IIIg) (see scheme 2) so as to obtain the compound (IV'g).

The deprotection of the silylated groups (TMDMS) is achieved with tetrabutyl ammonium fluoride (TBAF).

(3S,9S,14aR)-9-benzyl-3-((R)-7-hydroxy-6-oxooc-tyl)-6,6-dimethyldecahydropyrrolo[1,2-a][1,4,7,10]tetraazacyclododecine-1,4,7,10-tetraone (IV'f)

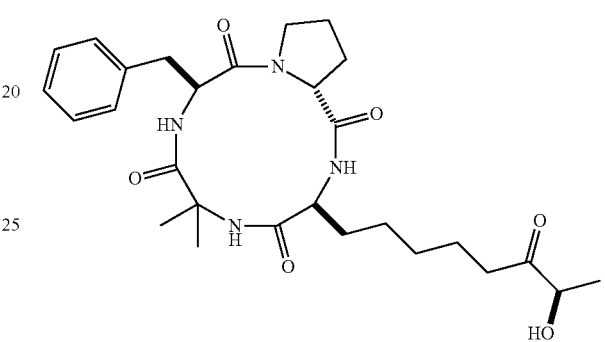

$R_f$=0.16 (2% MeOH/CH$_2$Cl$_2$); $^1$H NMR (400 MHz, CDCl$_3$) δ ppm 1.26-1.35 (m, 4H), 1.34 (s, 3H), 1.38 (d, J=7.1 Hz, 3H), 1.60-1.69 (m, 4H), 1.77 (m, 1H), 1.77 (s, 3H), 2.18 (m, 1H), 2.33 (m, 1H), 2.40-2.57 (m, 2H), 2.95 (dd, J=13.5, 5.7 Hz, 1H), 3.21 (m, 1H), 3.27 (dd, J=13.5, 10.1 Hz, 1H), 3.86 (m, 1H), 4.19 (m, 1H), 4.24 (q, J=7.1 Hz, 1H), 4.66 (bd, J=7.7 Hz, 1H), 5.17 (ddd, J=10.1, 10.1, 5.8 Hz, 1H), 6.00 (s, NH), 7.13 (d, J=10.2 Hz, NH), 7.18-7.30 (m, 5H), 7.51 (d, J=10.2 Hz, NH); $^{13}$C NMR (100 MHz, CDCl$_3$) δ ppm 20.1 (CH$_3$), 23.5 (CH$_2$), 23.8 (CH$_3$), 25.0 (CH$_2$), 25.2 (CH$_2$), 25.4 (CH$_2$), 26.7 (CH$_3$), 28.9 (CH$_2$), 29.0 (CH$_2$), 36.0 (CH$_2$), 37.5 (CH$_2$), 47.2 (CH$_2$), 53.7 (CH), 54.5 (CH), 58.0 (CH), 59.0 (C), 72.8 (CH), 126.9 (CH), 128.8 (2×CH), 129.2 (2×CH), 137.2 (C), 172.1 (C), 173.0 (C), 174.5 (C), 175.8 (C), 212.6 (C); Mass (ESI+) m/z (%) 551 (100) [M+Na]$^+$, 529 (10); HRMS (ESI+): m/z calculated for C$_{28}$H$_{40}$N$_4$O$_6$Na, 551.2846. found 551.2847.

(3S,9S,14aR)-9-benzyl-3-((s)-7-hydroxy-6-oxooc-tyl)-6,6-dimethyldecahydropyrrolo[1,2-a][1,4,7,10]tetraazacyclododecine-1,4,7,10-tetraone (IV'g)

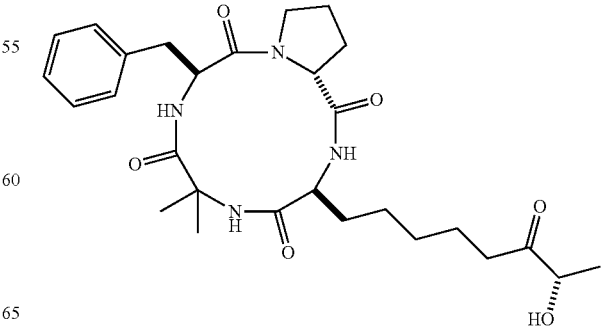

$R_f$=0.09 (60% EtOAc/cyclohexane); $^1$H NMR (400 MHz, CDCl$_3$) δ ppm 1.25-1.35 (m, 4H), 1.34 (s, 3H), 1.38 (d, J=7.1 Hz, 3H), 1.62-1.69 (m, 4H), 1.77 (m, 1H), 1.77 (s, 3H), 2.17 (m, 1H), 2.32 (m, 1H), 2.38-2.58 (m, 2H), 2.95 (dd, J=13.5, 5.7 Hz, 1H), 3.22 (m, 1H), 3.26 (dd, J=13.5, 10.1 Hz, 1H), 3.86 (m, 1H), 4.19 (m, 1H), 4.22 (q, J=7.1 Hz, 1H), 4.67 (bd, J=7.7 Hz, 1H), 5.16 (ddd, J=10.1, 10.1, 5.8 Hz, 1H), 6.12 (bs, NH), 7.17 (d, J=10.2 Hz, NH), 7.20-7.30 (m, 5H), 7.54 (d, J=10.2 Hz, NH); $^{13}$C NMR (100 MHz, CDCl$_3$) δ ppm 20.1 (CH$_3$), 23.5 (CH$_2$), 23.8 (CH$_3$), 25.0 (CH$_2$), 25.2 (CH$_2$), 25.5 (CH$_2$), 26.7 (CH$_3$), 28.9 (CH$_2$), 29.0 (CH$_2$), 36.0 (CH$_2$), 37.5 (CH$_2$), 47.2 (CH$_2$), 53.7 (CH), 54.5 (CH), 58.0 (CH), 59.0 (C), 72.8 (CH), 126.9 (CH), 128.8 (2×CH), 129.2 (2×CH), 137.2 (C), 172.1 (C), 173.0 (C), 174.5 (C), 175.8 (C), 212.6 (C); Mass (ESI+) m/z (%) 551 (45) [M+Na]$^+$, 242 (100); HRMS (ESI+): m/z calculated for C$_{28}$H$_{40}$N$_4$O$_6$Na, 551.2846. found 551.2847.

5. Other Cyclic Peptides and Preparation Method According to the Invention

Preparation of Cyclic Peptides (IV'j) and (IV'k)

The acid (IV'j) is obtained by catalytic hydrogenation. Hydroxamic acid (IV'k) is obtained from (IV'j).

Preparation of the cyclic peptide (3S,9S,14aR)-9-benzyl-3-(7-bromo-6-oxoheptyl)-6,6-dimethyl-decahydropyrrolo[1,2-a][1,4,7,10]tetraazacyclododecine-1,4,7,10-tetraone (IV$_h$)

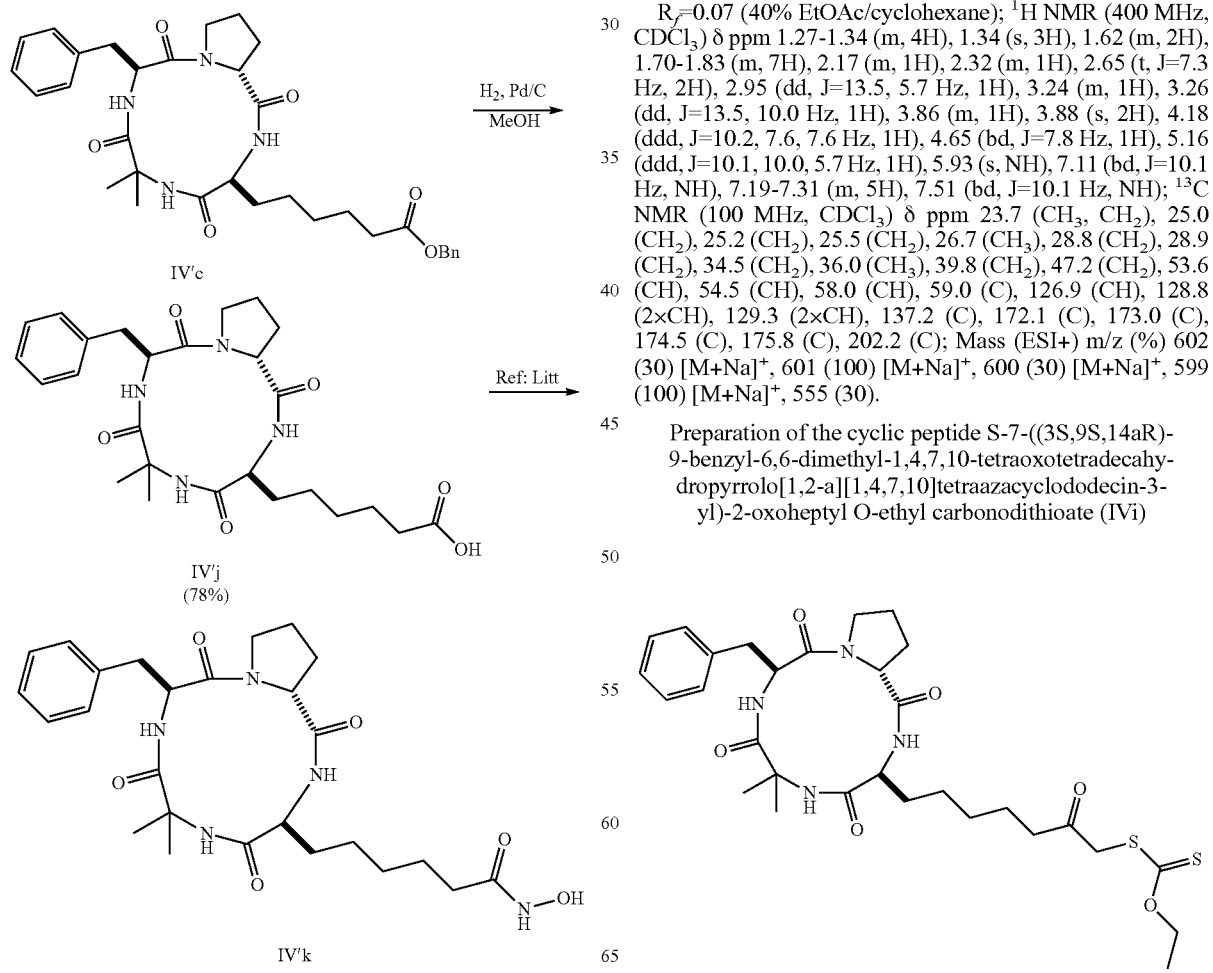

LiBr (23 mg, 0.27 mmol) is added to the compound (IV'a) (7.1 mg, 0.013 mmol) dissolved in acetone (1 mL) under argon. The solution is stirred away from light for 5 days. The acetone is evaporated and EtOAc is added. The organic phase is washed with water, dried on MgSO$_4$, and then evaporated. After flash chromatography (silica gel, 2% MeOH/CH$_2$Cl$_2$), the product (IVh) (5.8 mg, 75%) is isolated as a colorless lacquer.

$R_f$=0.07 (40% EtOAc/cyclohexane); $^1$H NMR (400 MHz, CDCl$_3$) δ ppm 1.27-1.34 (m, 4H), 1.34 (s, 3H), 1.62 (m, 2H), 1.70-1.83 (m, 7H), 2.17 (m, 1H), 2.32 (m, 1H), 2.65 (t, J=7.3 Hz, 2H), 2.95 (dd, J=13.5, 5.7 Hz, 1H), 3.24 (m, 1H), 3.26 (dd, J=13.5, 10.0 Hz, 1H), 3.86 (m, 1H), 3.88 (s, 2H), 4.18 (ddd, J=10.2, 7.6, 7.6 Hz, 1H), 4.65 (bd, J=7.8 Hz, 1H), 5.16 (ddd, J=10.1, 10.0, 5.7 Hz, 1H), 5.93 (s, NH), 7.11 (bd, J=10.1 Hz, NH), 7.19-7.31 (m, 5H), 7.51 (bd, J=10.1 Hz, NH); $^{13}$C NMR (100 MHz, CDCl$_3$) δ ppm 23.7 (CH$_3$, CH$_2$), 25.0 (CH$_2$), 25.2 (CH$_2$), 25.5 (CH$_2$), 26.7 (CH$_3$), 28.8 (CH$_2$), 28.9 (CH$_2$), 34.5 (CH$_2$), 36.0 (CH$_3$), 39.8 (CH$_2$), 47.2 (CH$_2$), 53.6 (CH), 54.5 (CH), 58.0 (CH), 59.0 (C), 126.9 (CH), 128.8 (2×CH), 129.3 (2×CH), 137.2 (C), 172.1 (C), 173.0 (C), 174.5 (C), 175.8 (C), 202.2 (C); Mass (ESI+) m/z (%) 602 (30) [M+Na]$^+$, 601 (100) [M+Na]$^+$, 600 (30) [M+Na]$^+$, 599 (100) [M+Na]$^+$, 555 (30).

Preparation of the cyclic peptide S-7-((3S,9S,14aR)-9-benzyl-6,6-dimethyl-1,4,7,10-tetraoxotetradecahydropyrrolo[1,2-a][1,4,7,10]tetraazacyclododecin-3-yl)-2-oxoheptyl O-ethyl carbonodithioate (IVi)

Potassium ethyl xanthate (4.2 mg, 0.026 mmol) in acetone (0.2 mL) is injected into a solution of compound (IV'a) (7.9 mg, 0.0147 mmol) in acetone (0.4 mL) at 0° C. The reaction is stirred at room temperature for 5 h. The solvent is evaporated and the residue is directly purified by flash chromatography in order to obtain the compound (IVi) (5.5 mg, 60%).

$R_f$=0.07 (40% EtOAc/cyclohexane); $^1$H NMR (400 MHz, CDCl$_3$) δ ppm 1.28-1.34 (m, 4H), 1.34 (s, 3H), 1.42 (t, J=7.1 Hz, 3H), 1.59-1.68 (m, 4H), 1.77 (m, 1H), 1.77 (s, 3H), 2.17 (m, 1H), 2.32 (m, 1H), 2.59 (t, J=7.3 Hz, 2H), 2.95 (dd, J=13.5, 5.7 Hz, 1H), 3.23 (m, 1H), 3.26 (dd, J=13.5, 9.9 Hz, 1H), 3.86 (m, 1H), 4.17 (m, 1H), 4.65 (bd, J=7.1 Hz, 2H), 6.67 (m, 1H), 5.16 (ddd, J=10.1, 10.1, 5.8 Hz, 1H), 5.88 (s; NH), 7.09 (d, J=10.2 Hz, NH), 7.18-7.29 (m, 5H), 7.50 (d, J=10.2 Hz, NH); $^{13}$C NMR (100 MHz, CDCl$_3$) δ ppm 23.6 (CH$_2$), 23.8 (CH$_3$), 25.0 (CH$_2$), 25.3 (CH$_2$), 25.5 (CH$_2$), 26.7 (CH$_3$), 28.9 (CH$_2$), 29.0 (CH$_2$), 36.0 (CH$_2$), 41.9 (CH$_2$), 45.7 (CH$_2$), 47.2 (CH$_2$), 53.7 (CH), 54.5 (CH), 58.0 (CH), 59.0 (C), 71.1 (CH$_2$), 126.9 (CH), 128.8 (2×CH), 129.2 (2×CH), 137.2 (C), 172.0 (C), 173.0 (C), 174.5 (C), 175.8 (C), 203.4 (C), 213.1 (C); Mass (ESI+) m/z (%) 641 (100) [M+Na]$^+$, 553 (85); HRMS (ESI+): m/z calculated for C$_{30}$H$_{42}$N$_4$O$_6$NaS$_2$ 641.2443. found 641.2438.

6. Biological Tests on Cells

The synthesized cyclic peptides were subject to tests in vitro on human fibroblasts infected by *Toxoplasma gondii* (Toxo), on non-infected human fibroblasts (HFF) and on HeLa cancer cells (cervical cancer) and MCF-7 cancer cells (breast cancer). Their respective efficiencies were tested at 90 nM as a preliminary test. The results are illustrated in Figure 1.

Correspondence of the molecules: API=Apicidine, 370=(IV'f), 338=(VI), 343=(IVc), 345=(IV'c), 347=(IV'j), 348=(IV'k), 350=(IVa), 351=(IV'a), 355=(IVg), 356=(IV'g), 357=(IV'g), 368=(IVf), 369=(IV'f), 397=(XVIIIa), 417=(IV'd), 418=(IV'b), 421=(IV'e).

The efficiency of the cyclic peptide (IV'$_f$) having shown interesting preliminary results, on human fibroblasts infected by *Toxoplasma gondii*, was then compared with that of other known molecules (apicidin and pyrimethamine notably).

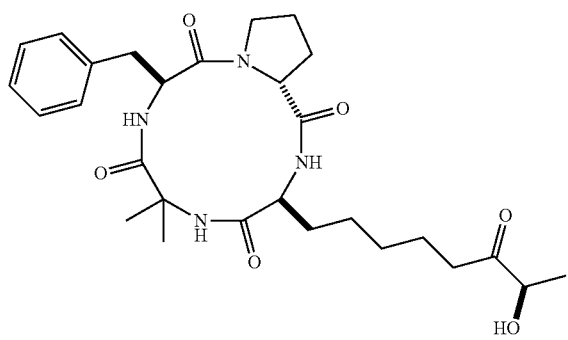

As illustrated in Figure 2, the compound (IV'f) showed very good effectiveness, of the order of the nanomolar. It has an activity close to that of apicidin and especially a much greater efficiency relatively to pyrimethamine which is the compound presently used in the treatment of toxoplasmosis. The table below gives the obtained numerical values.

| Compound (IV'$_f$) | Toxo | HFF | HeLa | MCF-7 |
|---|---|---|---|---|
| EC$_{50}$ (nM) | 28.6 | 647 | 474 | 533 |
| EC$_{90}$ (nM) | 79.7 | 4110 | 1012 | n.d. |

7. Biological Tests on Murine Brains

The cyclic peptide (IV'f) was then tested on cysts (bradyzoite form) of murine brains ex vivo at 200 nM (Figure 3). The cysts after treatment for 7 days with the cyclic peptide (IV'f) were re-inoculated intraperitonally to the mice. The mice having undergone the injection of cysts only treated with the saline phosphate buffer (PBS) or DMSO developed cysts, while those having undergone an injection of cysts treated with the cyclic peptide (IV'f) do not exhibit any cyst.

The invention claimed is:

1. A method for preparing a cyclic peptide of formula (I):

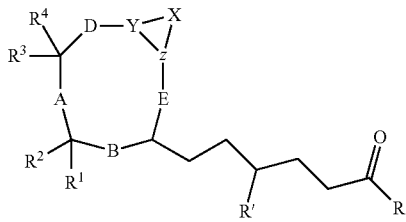

wherein
Y and Z, either identical or different, represent a carbon or nitrogen atom, Y and Z being optionally connected together through a double bond,
X represents 3 or 4 carbon, nitrogen and/or oxygen atoms optionally substituted,
A represents a group $R^5{}_a$—(N—CO)$_b$—$R^6{}_c$
B represents a group $R^7{}_d$—(N—CO)$_e$—$R^8{}_f$
D represents a group $R^9{}_g$—(N—CO)$_h$—$R^{10}{}_i$ or $R^9{}_g$—(CO)$_h$—$R^{10}{}_i$
E represents a group $R^{11}{}_j$—(N—CO)$_k$—$R^{12}{}_l$
wherein $R^5$, $R^6$, $R^7$, $R^8$, $R^9$, $R^{10}$, $R^{11}$, $R^{12}$, either identical or different, represent one or two or three carbon, nitrogen or oxygen atoms,
wherein a, b, c, d, e, f, g, h, i, j, k and l, either identical or different, are selected from 0, 1, 2 or 3, provided that the number of atoms of the ring is comprised between 12 and 16,
R represents H; OH; SH; an amine group; an alkyl, haloalkyl or heteroalkyl group containing between 1 and 10 carbon atoms as a linear or branched chain; an alkenyl or alkynyl group containing between 2 and 10 carbon atoms as a linear or branched chain; one or more cycloalkyl, cycloalkenyl or cycloalkynyl groups containing between 3 and 10 carbon atoms as a linear or branched chain; one or more aryl or heteroaryl groups containing between 3 and 10 carbon atoms per ring; an alkaryl or aralkyl group containing between 1 and 10 carbon atoms, the terms aryl and alkyl having the definitions above; an alkoxy, thioalkyl, sulfonylalkyl, aminoalkyl groups containing between 1 and 10 carbon atoms as a linear or branched chain; an alkoxyalkyl, alkylthioalkyl, alkylsulfonylalkyl, alkylaminoalkyl group containing between 1 and 30 carbon atoms as a linear or branched chain; one or more heterocyclic groups containing between 5 and 10 carbon atoms per ring;

R' represents H or a xanthate group of formula S—CS—O—R'''; wherein R''' represents H; an alkyl or haloalkyl group containing between 1 and 10 carbon atoms, as a linear or branched chain;

R$^1$, R$^2$, R$^3$ and R$^4$, either identical or different, represent H; OH, SH; an amine group; an alkyl, haloalkyl or heteroalkyl group containing between 1 and 30 carbon atoms as a linear or branched chain; an alkenyl or alkynyl group containing between 2 and 30 carbon atoms as a linear or branched chain; one or more cycloalkyl, cycloalkenyl or cycloalkynyl groups containing between 3 to 30 carbon atoms as a linear or branched chain; one or more aryl or heteroaryl groups containing between 3 to 10 carbon atoms per ring; an alkaryl or aralkyl group containing between 1 and 30 carbon atoms, the terms aryl and alkyl having the definitions above; an alkoxy, thioalkyl, sulfonylalkyl, aminoalkyl group containing between 1 and 30 carbon atoms as a linear or branched chain; an alkoxyalkyl, alkylthioalkyl, alkylsulfonylalkyl, alkylaminoalkyl group containing between 1 and 30 carbon atoms as a linear or branched chain; one or more heterocyclic groups containing between 5 and 10 atoms per cycle, either saturated or unsaturated, comprising at least one heteroatom selected from N, O and S, said heterocyclic group(s) may be substituted, and directly or indirectly bound by a bivalent alkylene radical to the ring of said peptide, wherein an intermediate compound of formula (II) is reacted:

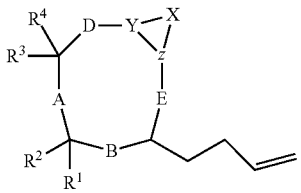

wherein X, Y, Z, A, B, D, E, R$^1$, R$^2$, R$^3$ and R$^4$ are as defined above, with a carbonyl xanthate of formula (III):

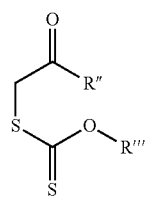

wherein

R'' represents H; an amine group; an alkyl, haloalkyl or heteroalkyl group containing between 1 and 10 carbon atoms as a linear or branched chain; an alkenyl or alkynyl group containing between 2 and 10 carbon atoms as a linear or branched chain; one or more cycloalkyl, cycloalkenyl or cycloalkynyl groups containing between 3 to 10 carbon atoms as a linear or branched chain; one or more aryl or heteroaryl groups containing between 3 to 10 carbon atoms per ring; an alkaryl or aralkyl group containing between 1 and 10 carbon atoms, the aryl and alkyl terms having the definitions above; an alkoxy, thioalkyl, sulfonylalkyl, aminoalkyl group containing between 1 and 10 carbon atoms as a linear or branched chain; an alkoxyalkyl, alkylthioalkyl, alkylsulfonylalkyl, alkylaminoalkyl group containing between 1 and 10 carbon atoms as a linear or branched chain; one or more heterocyclic groups containing between 5 and 10 carbon atoms per ring;

R''' represents H; an alkyl or haloalkyl group containing between 1 and 10 carbon atoms as a linear or branched chain;

and in that, optionally in a second step, it is proceeded with deprotection of the obtained compound.

2. The method according to claim 1, wherein the group R of the compound of formula (I) represents H; OH; SH; an alkyl or haloalkyl group containing between 1 and 10 carbon atoms as a linear or branched chain; one or more aryl or hetero-aryl groups containing between 3 and 10 carbon atoms per ring; an alkoxy, thioalkyl, sulfonylalkyl, aminoalkyl group containing between 1 and 10 carbon atoms as a linear or branched chain; one or more heterocyclic groups containing between 5 and 10 carbon atoms per ring.

3. The method according to claim 2, wherein the group R of the compound of formula (I) is selected from CH$_2$Cl, CH$_2$Br, CF$_3$, OH, O—CH$_2$—C$_6$H$_6$, NHOH, CH$_2$—S—CS—O—CH$_2$CH$_3$, CH$_2$CH$_3$, CO—CH$_2$CO$_2$—CH$_2$CH$_3$, CHOH—CH$_3$, CH(OTBDMS)CH$_3$.

4. The method according to claim 1, wherein the group R' of the compound of formula (I) represents H.

5. The method according to claim 1, wherein the group R'' of the compound of formula (III) represents H; an alkyl or haloalkyl group containing between 1 and 10 carbon atoms as a linear or branched chain; one or more aryl or hetero-aryl groups containing between 3 to 10 carbon atoms per ring; an alkoxy, thioalkyl, sulfonylalkyl, aminoalkyl group containing between 1 and 10 carbon atoms as a linear or branched chain; one or more heterocyclic groups containing between 5 and 10 carbon atoms per ring.

6. The method according to claim 5, wherein the group R'' of the compound of formula (III) is selected from CH$_2$Cl, CH$_2$Br, CF$_3$, O—CH$_2$—C$_6$H$_6$, CH$_2$CH$_3$, COCH$_2$CO$_2$Et, CH(OTBDMS)CH$_3$.

7. The method according to claim 1, wherein b=1; e=1; h=0; k=1.

8. The method according to claim 1 for preparing a cyclic peptide of formula (IV):

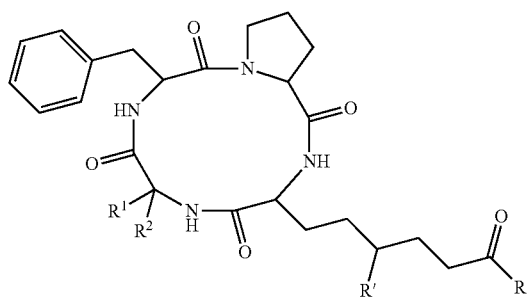

wherein R, R', R$^1$ and R$^2$ are as defined according to claim 1, wherein an intermediate compound of formula (V) is reacted:

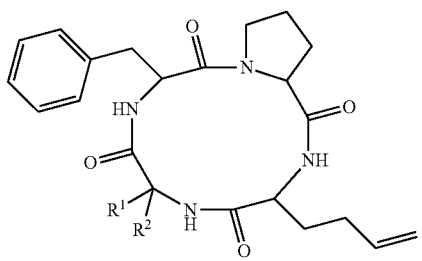

with a carbonyl xanthate of formula (III):

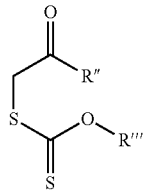

wherein R" and R'" are as defined in claim 1,
and in that, optionally in a second step, it is proceeded with deprotection of the obtained compound.

9. An intermediate synthesis compound of formula (V):

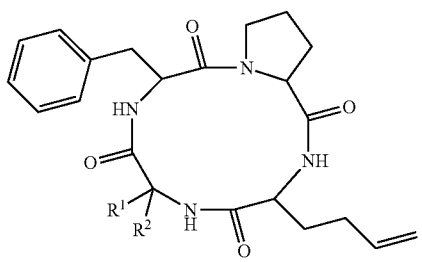

wherein $R^1$ and $R^2$ represents $CH_3$, or at least one of $R^1$ and $R^2$ represents $CH_2C\equiv CH$, the other of $R^1$ and $R^2$ representing H.

10. The cyclic peptide of formula (IV):

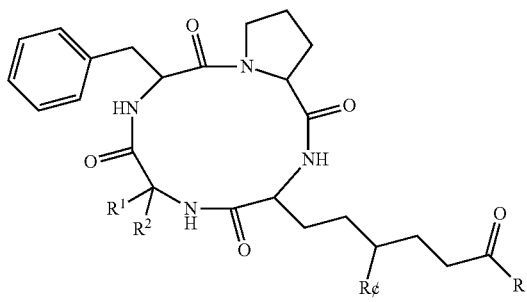

wherein

R represents H; OH; SH; an amine group; an alkyl, haloalkyl or heteroalkyl group containing between 1 and 10 carbon atoms as a linear or branched chain; an alkenyl or alkynyl group containing between 2 and 10 carbon atoms as a linear or branched chain; one or more cycloalkyl, cycloalkenyl or cycloalkynyl groups containing between 3 and 10 carbon atoms as a linear or branched chain; one or more aryl or heteroaryl groups containing between 3 and 10 carbon atoms per ring; an alkaryl or aralkyl group containing between 1 and 10 carbon atoms, the terms aryl and alkyl having the definitions above; an alkoxy, thioalkyl, sulfonylalkyl, aminoalkyl groups containing between 1 and 10 carbon atoms as a linear or branched chain; an alkoxyalkyl, alkylthioalkyl, alkylsulfonylalkyl, alkylamino alkyl group containing between 1 and 30 carbon atoms as a linear or branched chain; one or more heterocyclic groups containing between 5 and 10 carbon atoms per ring;

R' represents H or a xanthate group of formula S—CS—O—R'"; wherein R'" represents H; an alkyl or haloalkyl group containing between 1 and 10 carbon atoms, as a linear or branched chain;

$R^1$ and $R^2$ represent $CH_3$ or at least one of $R^1$ and $R^2$ represents $CH_2C\equiv CH$ or a heterocycle with 5 atoms selected from C, N and O, said heterocycle being bound by a methylene radical to the ring of said peptide, the other of R1 and R2 representing H.

11. The cyclic peptide according to claim 10, wherein R' represents H.

12. The peptide according to claim 10, wherein one of the hetero-atoms is substituted with a group selected from amino acids and peptides.

13. The cyclic peptide according to claim 10, wherein R represents CHOH—$CH_3$.

14. A method of treating an infection by a parasite comprising administering to a subject infected by the parasite an effective amount of the peptide according to claim 10.

15. The method according to claim 14, wherein the infection by a parasite comprises malaria, la toxoplasmosis, la coccidiosis, cryptosporidiosis or neosporosis.

16. A method of treating cancer comprising administering to a subject the peptide according to claim 10.

17. A method of treating an organ ex vivo before transplantation comprising delivering the peptide according to claim 10 to the organ.

* * * * *